US006794166B2

(12) United States Patent (10) Patent No.: US 6,794,166 B2
Godfroid et al. (45) Date of Patent: Sep. 21, 2004

(54) IDENTIFICATION AND MOLECULAR CHARACTERIZATION OF PROTEINS, EXPRESSED IN THE *IXODES RICINUS* SALIVARY GLANDS

(75) Inventors: Edmond Godfroid, Brussels (BE); Alex Bollen, Itterbeek (BE); Gérard Leboulle, Brussels (BE)

(73) Assignee: Henogen, S.A., Charleroi (BE)

( * ) Notice: Subject to any disclaimer, the term of this patent is extended or adjusted under 35 U.S.C. 154(b) by 0 days.

(21) Appl. No.: 09/910,430

(22) Filed: Jul. 19, 2001

(65) Prior Publication Data

US 2002/0127235 A1 Sep. 12, 2002

Related U.S. Application Data

(63) Continuation-in-part of application No. PCT/BE00/00061, filed on Jun. 6, 2000.

(30) Foreign Application Priority Data

Jun. 9, 1999 (GB) .............................................. 9913425

(51) Int. Cl.[7] .................................................. C12N 9/00
(52) U.S. Cl. ...................... 435/183; 424/184.1; 435/975
(58) Field of Search ................................ 435/183, 975; 424/184.1; 530/350

(56) References Cited

PUBLICATIONS

Ngo et al, The Protein Folding Problem and Tertiary Structure Prediction, 1994, pp. 492–495.*
Skolnide et al, Tibtech, vol. 18 pp. 34–39, 2000.*
Needham, et al. (1989) Characterization of Ixodid Tick Salivary–Gland Gene Products, Using Recombinant DNA Technology. Experimental & Applied Acarology, 7: 21–32.
Bior, et al. Differentially Expressed Genes in Tick Salivary Glands.
Das, et al. (2000) SALP16, A Gene induced in Ixodes Scapularis Salivary Glands During Tick Feeding. Am.J. Trop. Med. Hyg. 62(1) 99–105.
Luo, et al. (1997) Cloning and sequence of a gene for the homologue of the stearoyl CoA desaturase from salivary glands of the tick *Amblyomma americanum*. Insect Molecular Biology 6(3): 267–271.
International Search Report from PCT/BE00/00061 filed Jun. 6, 2000.
Bergman, D.K., et al. (2000) Isolation and molecular cloning of a secreted immunosuppressant protein from *Dermacentor andersoni* salivary gland. J. Parasitol. 86(3):516–525.
Brossard, M., et al. (1997)Immunology of interactions between ticks and hosts. Medical and Veterinary Entomology 11:270–276.
De Silva, A. M., et al. (1995) Growth and Migration of *Borrelia burgdorferi* In Ixodes Ticks during blood feeding. Am. J. Trop. Med. Hyg. 53(4):397–404.
Frohman, M.A., et al. (1988) Rapid production of full–length cDNAs from rare transcripts: Amplification using a single gene–specific oligonucleotide primer. Proc. Natl. Acad. Sci. USA 85:8998–9002.

Fuchsberger, N., et al. (1995) Ixodid tick salivary gland extracts inhibit production of lipopolysaccharide–induced mRNA of several different human cytokines. Experimental & Applied Acarology 19:671–676.
Ganapamo, F., et al. (1995) In vitro production of interleukin–4 and interferon–γ by lymph node cells from BALB/c mice infested with nymphal *Ixodes ricinus* ticks. Immunology 85:120–124.
Ganapamo, F., et al. (1996) Immunosuppression and cytokine production in mice infected with *Ixodes ricinus* ticks: a possible role of laminin and interleukin–10 on the in vitro responsiveness of lymphocytes to mitogens. Immunology 87:259–263.
Ganapamo, F., et al. (1997) Identification of an *Ixodes ricinus* salivary gland fraction through its ability to stimulate CD4 T cells present in BALB/c mice lymph nodes draining the tick fixation site. Parasitology 775:91–96.
Hubank, M., et al. (1994) Identifying differences in mRNA expression by representational difference analysis of cDNA. Nucleic Acids Research 22(25):5640–5648.
Kopecky, J., et al. (1998) Suppressive effect of *Ixodes ricinus* salivary gland extract on mechanisms of natural immunity in vitro. Parasite Immuniology 20:169–174.
Ramachandra R.N., et al. (1992) Modulation of host–immune responses by ticks (Acari:Ixodidae): effect of salivary gland extracts on host macrophages and lymphocyte cytokine production. J. Med. Entomol. 29(5):818–826.
Sauer, J.R., et al. (1995) Tick Salivary Gland Physiology. Ann. Rev. Entomol. 40:245–267.
Schoeler, G.B., et al. (2000) Influence of soluble proteins from the salivary glands of ixodes ticks on the in–vitro proliferative responses of lymphocytes from BALB/c and C3H/HeN mice. Ann. Trop. Med. Parasitol. 94(5):507–518.
Urioste, S, et al. (1994) Saliva of the Lyme Disease Vector, *Ixodes dammini*, Blocks Cell Activation by a Nonprostaglandin $E_2$–dependent Mechanism. J. Exp. Med. 180:1077–1085.
Wang, H., et al. (1994) Excretion of host immunoglobulin in tick saliva and detection if IgG–binding proteins in tick haemolymph and salivary glands. Parasitology 109:525–530.
Wikel, S. K. (1996) Host Immunity to Ticks. Annu. Rev. Entomol 41:1–22.
Zeidner, et al. (1996) Suppression of Acute *Ixodes scapularis*–Induced *Borrelia burgdorferi* Infection using Tumor Necrosis Factor–α, Interleukin–2, and Interferon–γ. J. Infect. Diseases 173:187–195.

* cited by examiner

*Primary Examiner*—Patrick J. Nolan
(74) *Attorney, Agent, or Firm*—Knobbe, Martens, Olson & Bear, LLP

(57) ABSTRACT

The invention relates to new polynucleotides which encode polypeptides expressed in the salivary glands of ticks, more particularly the *Ixodes ricinus* arthropod tick, during the slow-feeding phase of the blood meal have. Said polynucleotides and related polynucleotides may be used in different constructions and for different applications which are also included in said invention.

12 Claims, 9 Drawing Sheets

SEQUENCE LISTING

<160> NUMBER OF SEQ ID NOS: 34

<210> SEQ ID NO 1
<211> LENGTH: 194
<212> TYPE: DNA
<213> ORGANISM: Ixodes ricinus

<400> SEQUENCE: 1

```
ataccttcca cttgtagccc ttcctcatcc gatatggtga cggatgccat tgcatcctcg      60
tcgtggaaga ggtcctcttc taaataagac ccatccatat atgtgtgttt gcgaatgccg     120
tcgacgtagc tcctgactag aaactcgtcg gctaggacag aacttttctt caggtttagc     180
gtaatgtcct cgtt                                                       194
```

<210> SEQ ID NO 2
<211> LENGTH: 607
<212> TYPE: DNA
<213> ORGANISM: Ixodes ricinus
<220> FEATURE:
<221> NAME/KEY: misc_feature
<222> LOCATION: (1)...(607)
<223> OTHER INFORMATION: n = A,T,C or G

<400> SEQUENCE: 2

```
taccngggaa tccaaaacca atttttattg gaacttccac gtcttcttca aggcggtggc      60
acctctgcat ttatgaagtt cgtcttggca ttttattttt tgcttctttc attgcrgaac     120
tcgcaaatgc acttcccgtg cttgtcgcat ttcgcccaa aagcgcatgg cattccttcc     180
ggcagattaa cttttcaaa ttcacggttc tgaaccaata atagatcgtg gcaatgtttg     240
tgctgtttgc gatttgcaaa ccagctgtag ccaccattgg actcaaaggt gcgcacaaca     300
tggcgccgaa ctgtgaaaaa caaattaagg ctnctttgta ataacgctag tcttggtacg     360
ccgttagagg tcgatgtcgc gcctcgcgat tgcaaagtca cttgcactta tcaagctcct     420
ggagaaaaat gggtgcaacg gggggatcag cgtttgtact tgcaaacatt tgtggagacg     480
gtaaaccwgt atttcgcgga actcagatgc tccagcgtga agctcgtctt aataaaagtt     540
gtaaattcga gtatngatga agaactgaaa ttcgaggcat ttagaaacac cacgagaagc     600
agcggaa                                                               607
```

<210> SEQ ID NO 3
<211> LENGTH: 259
<212> TYPE: DNA
<213> ORGANISM: Ixodes ricinus

```
<400> SEQUENCE: 3
gatcctacgc ctgaaaatga gtgtccatcg tcttcacata gtgccacatt gtaattggta      60
caagctccat tttcgtcagc gctgtttgtt atgctgccgc ctactttttcc ttcggcactc    120 cataagttaa accctgtcat tataagtgtg attgccgtat ctcggctgaa tgggttccat    180
ttttctctta aataatcacg tgtccatatt ccatgtattg tgttcatgag tatgtgattc    240
tcatcgtata tcttcgcct                                                  259

<210> SEQ ID NO 4
<211> LENGTH: 170
<212> TYPE: DNA
<213> ORGANISM: Ixodes ricinus

<400> SEQUENCE: 4
ccactcgaaa atggaggctt tgaaacattt cagtacccct gtgaactctg gctttgcaat      60
gtaacagcaa aaacacttac agttgaaggg tgcagtgtca gacgctatgg aagttgcatc    120
cacgagcacr accctgatta ctactggcca cgttgctrtc cgggtcgtcc                170

<210> SEQ ID NO 5
<211> LENGTH: 168
<212> TYPE: DNA
<213> ORGANISM: Ixodes ricinus

<400> SEQUENCE: 5
gtatgttacc atgtccaacc cggttattaa atacaccaag tcgtaggatt tgtaggcagc      60
tgcattgccc ttgacgtact ctctcaacgt tgccaaggac tcaggcccat aaatgtagtg    120
gggttgacct tgaactcttc gtaaaaagcg ttctttctcc gtcgtgag                  168

<210> SEQ ID NO 6
<211> LENGTH: 247
<212> TYPE: DNA
<213> ORGANISM: Ixodes ricinus

<400> SEQUENCE: 6
ccgaamataa aacttagtct caccaatata cgtttgccta acgcgaagga acaggcacaa      60
atatactacg agcacgacat tctcaagaac acggttcacg gagtgtggac gagaattcac    120
tcaaaatatc cgttccctga agatgaggga attacactga taatgacagg gtttgattta    180
tggagtgccg atttaactgt aggcggcacc ataacaaaca gcgctgagaa aagcggagct    240
tgtacga                                                               247

<210> SEQ ID NO 7
<211> LENGTH: 261
<212> TYPE: DNA
<213> ORGANISM: Ixodes ricinus
<220> FEATURE:
<221> NAME/KEY: CDS
<222> LOCATION: (1)..(258)

<400> SEQUENCE: 7 atg cct ttt att ttc gtg gtg agc tta gtc att gtg gcc tgc atc gtg       48
Met Pro Phe Ile Phe Val Val Ser Leu Val Ile Val Ala Cys Ile Val
 1               5                  10                  15 gta gac aca gcc aac cac aaa ggt aga ggg cgg cct gcg aag tgt aaa       96
Val Asp Thr Ala Asn His Lys Gly Arg Gly Arg Pro Ala Lys Cys Lys
             20                  25                  30
```

```
ctt cct ccg gac gac gga cca tgc aga gca cga att ccg agt tac tac      144
Leu Pro Pro Asp Asp Gly Pro Cys Arg Ala Arg Ile Pro Ser Tyr Tyr
         35                  40                  45 ttt gat aga aaa acc aaa acg tgc aag gag ttt atg tat ggc gga tgc      192
Phe Asp Arg Lys Thr Lys Thr Cys Lys Glu Phe Met Tyr Gly Gly Cys
 50                  55                  60 gaa gga aac gaa aac aat ttt gaa aac ata act acg tgc caa gag gaa      240
Glu Gly Asn Glu Asn Asn Phe Glu Asn Ile Thr Thr Cys Gln Glu Glu
 65                  70                  75                  80 tgc aga gca aaa aaa gtc tag                                          261
Cys Arg Ala Lys Lys Val
             85

<210> SEQ ID NO 8
<211> LENGTH: 86
<212> TYPE: PRT
<213> ORGANISM: Ixodes ricinus

<400> SEQUENCE: 8

Met Pro Phe Ile Phe Val Val Ser Leu Val Ile Val Ala Cys Ile Val
 1               5                  10                  15

Val Asp Thr Ala Asn His Lys Gly Arg Gly Arg Pro Ala Lys Cys Lys
             20                  25                  30

Leu Pro Pro Asp Asp Gly Pro Cys Arg Ala Arg Ile Pro Ser Tyr Tyr
         35                  40                  45

Phe Asp Arg Lys Thr Lys Thr Cys Lys Glu Phe Met Tyr Gly Gly Cys
 50                  55                  60

Glu Gly Asn Glu Asn Asn Phe Glu Asn Ile Thr Thr Cys Gln Glu Glu
 65                  70                  75                  80

Cys Arg Ala Lys Lys Val
             85

<210> SEQ ID NO 9
<211> LENGTH: 292
<212> TYPE: DNA
<213> ORGANISM: Ixodes ricinus

<400> SEQUENCE: 9
catcgmagcc atagtatatt ttgcacttgt cttccgtttc gtcgtagtag gaccgattcc      60
acattgtagt acaccagtca cttatatcct gcgggcggtg cttgcatttg tcctgaacaa     120
atcttccaca gcgcttgtcg cacgcctcct gggaatagaa cgcgttctct cctccgcatc     180
tccatttgga atcatagaaa catctttcag tttgaatatt gtagcgataa taatcggtat     240
cagtttcttt gcatggtcct gggaggggtt tggcgcaggg gccgtattca gg            292

<210> SEQ ID NO 10
<211> LENGTH: 270
<212> TYPE: DNA
<213> ORGANISM: Ixodes ricinus

<400> SEQUENCE: 10
ggtaatagtt gtcaaattcc attaatgtat cctgaaatgt gaccatatct ttgtttcccc      60
tgtaaaatct cataaaaggc tgtgtgtttt ccttaagaag tgtaacagcc acgatggtca     120
atctcacgga tggatgtgtg cactttttat atctcaggtt tgccgacatt gccattacag     180
ataaatagtt gataatttct ttcttgttat agttgtaagc agcgcatgtt gttgcatcaa     240
gcaccacatg cacttcaggc aatatggttt                                     270
```

<210> SEQ ID NO 11
<211> LENGTH: 316
<212> TYPE: DNA
<213> ORGANISM: Ixodes ricinus

<400> SEQUENCE: 11

```
agaaagcagt catattggcc atccacaggt cacaatggtt ctctccttga cctggcatcg      60
ggattcgaag tatggtgcag ttcacgtagt tggaatacaa cacgaaatgt gttcgttggt     120
acgccaatag gggttctcgc aaagaacata tcatttggag gaaggcgtag tccgtcgaga     180
tatcccaaaa ctagggtttc attgcgtgcg aaccaactgc ccccacttct gtatgtgtac     240
tgtaaggagt rgttgaacgg ygtcctcttt cccataacct tgaagttttc acactgcaga     300
ggattacctc tcaaaa                                                     316
```

<210> SEQ ID NO 12
<211> LENGTH: 241
<212> TYPE: DNA
<213> ORGANISM: Ixodes ricinus

<400> SEQUENCE: 12

```
aaggtagcaa gggtggtagg ctttcctcac aaagagtctg gcttccgtga taaccatatc      60
cattcctcac cgtatacccg tcatccaacg tcaattgtgt tacaaggcag ataatgtcaa     120
aatggctctg gtccctataa tagtcggata atgtagaaat cgctccatgt ggccaaatag     180
atgttcctct ttcatactgt tttaacttta attgtaggtc cgcctcgttc tcgaggtatg     240
t                                                                     241
```

<210> SEQ ID NO 13
<211> LENGTH: 636
<212> TYPE: DNA
<213> ORGANISM: Ixodes ricinus
<220> FEATURE:
<221> NAME/KEY: misc_feature
<222> LOCATION: (1)...(636)
<223> OTHER INFORMATION: n = A,T,C or G

<400> SEQUENCE: 13

```
ttccccnaat tggccttgcg anncttgcaa gtcgacncta gaggctccga agatggacag      60
attgcgcatg aaatatttga atcgagcag aatggtgatt ttaggagcga ttatattgtg     120
ccacccagtt tgaaagtgca agaacgcaca gtggtttacc gtaacaagta caccagagtt     180
cctgtaaatt ttaccgtcga agttgccatg ctgattgata agtatttata cwaggagttc     240
aagaacgaga gccacatcgt accgtacctg gctatgatac tgactttgat aaatctgagg     300
tatgccgaca cacatgaccc gtacatccag tttcttctca cacaagtgtt cgtggggaaw     360
wctggcgatc atatgggcca catgcccttc cgacgagcgt tcttgttcag gcgccggcat     420
tatgcgcagt ttaggcccaa tmacaccttc cacttgtaat tctccgttgt tggatagtgt     480
aagtgaggcc attgcatcag catcgtggaa gargccttcc tccaagtagg aaccgcccat     540
ttaggtttgc tttcccaatc cgccaattta antttaaaa aaaattcccc ccccaaaaat     600
taattttttt taaaggtgga ttgtgatttc tccgtt                               636
```

<210> SEQ ID NO 14
<211> LENGTH: 432
<212> TYPE: DNA
<213> ORGANISM: Ixodes ricinus

<400> SEQUENCE: 14

```
gatcccaaaa gtgccctgg arcgacggtt acatcatgag ctacgtcata aacttcaaaa        60
accacttcaa attttctccc tgctgtgtag aatcaattcg attcgtcgca cgagagcggg       120
actgcctcta caaagtcaat gccaaggatg ctgtaaaaag cctaatatct ctgcccggat       180
ttaggatatc gccaacgagt ttctgtcaat ttatgcatcc gctttaccgc ggtgtccata       240
gcgataagaa agcaggtctg tccgattgcg tacagacgtg tagaacggcc aaaaatcgac       300
gaggaggcta ccattcatgg attcacgcgg cacttgacgg ggttccttgc gacaagagaa       360
accccaagaa ggcctgcata aacgggaaat gcaccctcct taagagcatg ccccacagaa       420
cgtaccggga at                                                           432
```

<210> SEQ ID NO 15
<211> LENGTH: 466
<212> TYPE: DNA
<213> ORGANISM: Ixodes ricinus

<400> SEQUENCE: 15

```
agggcgttct ttgcttyaca gggaacrgca tatgggccac gtgaccttcc aatgaccgct        60
ccaaatctgg cataggttga aytcgcaagt cgtggcgcag caggcctycc acattcactc       120
catcctcgtc ttttaggatg actgccgcca tttgttttgt atcgtggtac aggtgtttgt       180
tatggtccga gccgtcgaca taagtattga ccaacgatcg gccgaatgat tacggctcac       240
caaacacatc aaatacccc gtcaagtcaa gagctggaag cacaaagcat agtatgtaca       300
agataccctt ggaaatcttt cccgaagttc accttgtggt ggacagcaca tttgccaaag       360
cttttaaatt tgacgtgtac aaagtaacgc gttacttcgc agtgcttaca aatgcggcta       420
atcttaggta tgccagcttc gtatttccaa aagtacagct caggat                      466
```

<210> SEQ ID NO 16
<211> LENGTH: 377
<212> TYPE: DNA
<213> ORGANISM: Ixodes ricinus

<400> SEQUENCE: 16

```
ctcgtccaca cattctccta aaatgcaagc ctttttttc ccacaaggtg taccgtcgac        60
tacactgagt ctccaataaa tatgttttcc ggtgcaattt accttgcagt ctttgacgcc       120
gtatgtaggg tcagcgtgca tgccttcgtc gtacatatac accctctgac agtagttgct       180
cagtgttgtc atcctaccag gaagcttaga cgaacgtttt attgtttttg tcgtgtatcg       240
ttctctaagg catttgaatt ccggacggtt gtagaggttc ctgacttctc gctggcagca       300
ataagagaac tgatactggc gctcgtcttg catcttgtaa ctcatgaggt atccgtcatc       360
ccatgggcag tccgcag                                                      377
```

<210> SEQ ID NO 17
<211> LENGTH: 1670
<212> TYPE: DNA
<213> ORGANISM: Ixodes ricinus
<220> FEATURE:
<221> NAME/KEY: CDS
<222> LOCATION: (54)..(1517)

<400> SEQUENCE: 17

```
aaggaagaag ttaggcgtag gctttgggaa accggtcatc ctcgaaacca gag atg       56
                                                           Met
                                                             1 tcg gga ctc agc ctg aaa ttg tgg att gta gcg ttc ttt tct ttc tgc     104
Ser Gly Leu Ser Leu Lys Leu Trp Ile Val Ala Phe Phe Ser Phe Cys
              5                  10                  15 ttg gcc gag aaa gag cat ggg atc gtg tac ccc agg atg ctt gaa agc     152
Leu Ala Glu Lys Glu His Gly Ile Val Tyr Pro Arg Met Leu Glu Ser
         20                  25                  30 aga gca gca act gga gag aga atg ctt aaa atc aac gat gac ctg acg     200
Arg Ala Ala Thr Gly Glu Arg Met Leu Lys Ile Asn Asp Asp Leu Thr
     35                  40                  45 ttg acg ctg cag aag agt aag gtc ttc gct gac gac ttt ctc ttc agc     248
Leu Thr Leu Gln Lys Ser Lys Val Phe Ala Asp Asp Phe Leu Phe Ser
 50                  55                  60                  65 acg acc gac gga att gaa cct att gat tac tac atc aaa gcc gaa gac     296
Thr Thr Asp Gly Ile Glu Pro Ile Asp Tyr Tyr Ile Lys Ala Glu Asp
                 70                  75                  80 gct gaa cgt gac atc tac cac gac gca act cac atg gca tca gta agg     344
Ala Glu Arg Asp Ile Tyr His Asp Ala Thr His Met Ala Ser Val Arg
             85                  90                  95 gta acg gac gat gat ggc gtg gaa gtg gaa gga att ctt gga gag agg     392
Val Thr Asp Asp Asp Gly Val Glu Val Glu Gly Ile Leu Gly Glu Arg
        100                 105                 110 ctt cgt gtt aaa cct ttg ccg gca atg gcc cgc agc agc gat ggc ctc     440
Leu Arg Val Lys Pro Leu Pro Ala Met Ala Arg Ser Ser Asp Gly Leu
    115                 120                 125 aga ccg cat atg ttg tac gaa gtc gac gca cac gaa aac ggc cgg cca     488
Arg Pro His Met Leu Tyr Glu Val Asp Ala His Glu Asn Gly Arg Pro
130                 135                 140                 145 cat gat tat ggt tca ccg aac aca aca aat acc ccc gta gag aga aga     536
His Asp Tyr Gly Ser Pro Asn Thr Thr Asn Thr Pro Val Glu Arg Arg
                150                 155                 160 gct gga ggc aca gaa ccc cag atg tac aag ata cca gcg gaa atc tat     584
Ala Gly Gly Thr Glu Pro Gln Met Tyr Lys Ile Pro Ala Glu Ile Tyr
            165                 170                 175 ccc gaa gtt tac ctt gtg gcg gat agt gcc ttt gcc aaa gaa ttt aac     632
Pro Glu Val Tyr Leu Val Ala Asp Ser Ala Phe Ala Lys Glu Phe Asn
        180                 185                 190 ttt gat gtg aac gcc gtt acg cgt tac ttc gca gtg ctt aca aat gcg     680
Phe Asp Val Asn Ala Val Thr Arg Tyr Phe Ala Val Leu Thr Asn Ala
    195                 200                 205 gct aat ctt agg tat gaa agc ttc aaa tct cca aag gta cag ctc agg     728
Ala Asn Leu Arg Tyr Glu Ser Phe Lys Ser Pro Lys Val Gln Leu Arg
210                 215                 220                 225 atc gtt ggc ata acg atg aac aaa aac cca gca gac gag cca tac att     776
Ile Val Gly Ile Thr Met Asn Lys Asn Pro Ala Asp Glu Pro Tyr Ile
                230                 235                 240 cac aat ata cgg gga tat gag cag tac cgg aat att ttg ttt aag gaa     824
His Asn Ile Arg Gly Tyr Glu Gln Tyr Arg Asn Ile Leu Phe Lys Glu
            245                 250                 255 aca ctg gag gat ttc aac act cag atg aag tca aaa cat ttt tat cgt     872
Thr Leu Glu Asp Phe Asn Thr Gln Met Lys Ser Lys His Phe Tyr Arg
        260                 265                 270 act gcc gat atc gtg ttt ctc gtg aca gca aaa aat atg tcc gaa tgg     920
Thr Ala Asp Ile Val Phe Leu Val Thr Ala Lys Asn Met Ser Glu Trp
    275                 280                 285
```

-continued

| | | |
|---|---|---|
| gtt ggt agc aca cta caa tca tgg act ggc ggg tac gct tac gta gga<br>Val Gly Ser Thr Leu Gln Ser Trp Thr Gly Gly Tyr Ala Tyr Val Gly<br>290                          295                          300                          305 | 968 |

```
gtt ggt agc aca cta caa tca tgg act ggc ggg tac gct tac gta gga      968
Val Gly Ser Thr Leu Gln Ser Trp Thr Gly Gly Tyr Ala Tyr Val Gly
290                 295                 300                 305 aca gcg tgt tcc gaa tgg aaa gta gga atg tgt gaa gac cga ccg aca     1016
Thr Ala Cys Ser Glu Trp Lys Val Gly Met Cys Glu Asp Arg Pro Thr
                310                 315                 320 agc tat tac gga gct tac gtt ttc gcc cat gag ctg gcg cat aat ttg     1064
Ser Tyr Tyr Gly Ala Tyr Val Phe Ala His Glu Leu Ala His Asn Leu
            325                 330                 335 ggt tgt caa cac gat gga gat ggt gcc aat agc tgg gtg aaa ggg cac     1112
Gly Cys Gln His Asp Gly Asp Gly Ala Asn Ser Trp Val Lys Gly His
        340                 345                 350 atc gga tct gcg gac tgc cca tgg gat gac gga tac ctt atg agc tac     1160
Ile Gly Ser Ala Asp Cys Pro Trp Asp Asp Gly Tyr Leu Met Ser Tyr
    355                 360                 365 aag atg gaa gac gag cgc cag tat aag ttt tct ccc tac tgc cag aga     1208
Lys Met Glu Asp Glu Arg Gln Tyr Lys Phe Ser Pro Tyr Cys Gln Arg
370                 375                 380                 385 gaa gtc agg aac ctc tac agg cgt ccg gaa ttc aaa tgc ctc act gaa     1256
Glu Val Arg Asn Leu Tyr Arg Arg Pro Glu Phe Lys Cys Leu Thr Glu
                390                 395                 400 cga aaa gcg aaa aaa aca atc cgc tcg tct aag cta cct ggt gtg atg     1304
Arg Lys Ala Lys Lys Thr Ile Arg Ser Ser Lys Leu Pro Gly Val Met
            405                 410                 415 aca tca tcg agc aac tat tgc cgg agg gtg tac atg tac gaa aaa ggc     1352
Thr Ser Ser Ser Asn Tyr Cys Arg Arg Val Tyr Met Tyr Glu Lys Gly
        420                 425                 430 atg cac gcc gac gag gca tat ggc gtc aag gac tgc agg gta aaa tgc     1400
Met His Ala Asp Glu Ala Tyr Gly Val Lys Asp Cys Arg Val Lys Cys
    435                 440                 445 acc aca aca tca aga atg tat tgg cta ctc ggt gta gtc gac ggt aca     1448
Thr Thr Thr Ser Arg Met Tyr Trp Leu Leu Gly Val Val Asp Gly Thr
450                 455                 460                 465 cct tgc gga aat gga aag gct tgc att ctt ggg aaa tgc agg aac aaa     1496
Pro Cys Gly Asn Gly Lys Ala Cys Ile Leu Gly Lys Cys Arg Asn Lys
                470                 475                 480 atc aaa ata agc aag aag gac tgagaggttg ataatatcaa attaatcatg       1547
Ile Lys Ile Ser Lys Lys Asp
            485 atatttcaac cacatgactt cgtgctcaac tggtagcccc aaataaattt taaaaaaaat   1607 cccaatatgc gtggtagaaa aagcagcaaa caataaaact tctaaaaatg tcttgcaaaa   1667 atg                                                                1670

<210> SEQ ID NO 18
<211> LENGTH: 488
<212> TYPE: PRT
<213> ORGANISM: Ixodes ricinus

<400> SEQUENCE: 18

Met Ser Gly Leu Ser Leu Lys Leu Trp Ile Val Ala Phe Phe Ser Phe
1               5                   10                  15

Cys Leu Ala Glu Lys Glu His Gly Ile Val Tyr Pro Arg Met Leu Glu
            20                  25                  30

Ser Arg Ala Ala Thr Gly Glu Arg Met Leu Lys Ile Asn Asp Asp Leu
        35                  40                  45

Thr Leu Thr Leu Gln Lys Ser Lys Val Phe Ala Asp Asp Phe Leu Phe
    50                  55                  60
```

-continued

Ser Thr Thr Asp Gly Ile Glu Pro Ile Asp Tyr Tyr Ile Lys Ala Glu
 65                  70                  75                  80

Asp Ala Glu Arg Asp Ile Tyr His Asp Ala Thr His Met Ala Ser Val
                 85                  90                  95

Arg Val Thr Asp Asp Gly Val Glu Val Glu Gly Ile Leu Gly Glu
            100                 105                 110

Arg Leu Arg Val Lys Pro Leu Pro Ala Met Ala Arg Ser Ser Asp Gly
        115                 120                 125

Leu Arg Pro His Met Leu Tyr Glu Val Asp Ala His Glu Asn Gly Arg
    130                 135                 140

Pro His Asp Tyr Gly Ser Pro Asn Thr Thr Asn Thr Pro Val Glu Arg
145                 150                 155                 160

Arg Ala Gly Gly Thr Glu Pro Gln Met Tyr Lys Ile Pro Ala Glu Ile
                165                 170                 175

Tyr Pro Glu Val Tyr Leu Val Ala Asp Ser Ala Phe Ala Lys Glu Phe
            180                 185                 190

Asn Phe Asp Val Asn Ala Val Thr Arg Tyr Phe Ala Val Leu Thr Asn
        195                 200                 205

Ala Ala Asn Leu Arg Tyr Glu Ser Phe Lys Ser Pro Lys Val Gln Leu
    210                 215                 220

Arg Ile Val Gly Ile Thr Met Asn Lys Asn Pro Ala Asp Glu Pro Tyr
225                 230                 235                 240

Ile His Asn Ile Arg Gly Tyr Glu Gln Tyr Arg Asn Ile Leu Phe Lys
                245                 250                 255

Glu Thr Leu Glu Asp Phe Asn Thr Gln Met Lys Ser Lys His Phe Tyr
            260                 265                 270

Arg Thr Ala Asp Ile Val Phe Leu Val Thr Ala Lys Asn Met Ser Glu
        275                 280                 285

Trp Val Gly Ser Thr Leu Gln Ser Trp Thr Gly Gly Tyr Ala Tyr Val
290                 295                 300

Gly Thr Ala Cys Ser Glu Trp Lys Val Gly Met Cys Glu Asp Arg Pro
305                 310                 315                 320

Thr Ser Tyr Tyr Gly Ala Tyr Val Phe Ala His Glu Leu Ala His Asn
                325                 330                 335

Leu Gly Cys Gln His Asp Gly Asp Gly Ala Asn Ser Trp Val Lys Gly
            340                 345                 350

His Ile Gly Ser Ala Asp Cys Pro Trp Asp Asp Gly Tyr Leu Met Ser
        355                 360                 365

Tyr Lys Met Glu Asp Glu Arg Gln Tyr Lys Phe Ser Pro Tyr Cys Gln
    370                 375                 380

Arg Glu Val Arg Asn Leu Tyr Arg Arg Pro Glu Phe Lys Cys Leu Thr
385                 390                 395                 400

Glu Arg Lys Ala Lys Lys Thr Ile Arg Ser Ser Lys Leu Pro Gly Val
                405                 410                 415

Met Thr Ser Ser Ser Asn Tyr Cys Arg Arg Val Tyr Met Tyr Glu Lys
            420                 425                 430

Gly Met His Ala Asp Glu Ala Tyr Gly Val Lys Asp Cys Arg Val Lys
        435                 440                 445

Cys Thr Thr Thr Ser Arg Met Tyr Trp Leu Leu Gly Val Val Asp Gly
450                 455                 460

```
Thr Pro Cys Gly Asn Gly Lys Ala Cys Ile Leu Gly Lys Cys Arg Asn
465                 470                 475                 480

Lys Ile Lys Ile Ser Lys Lys Asp
                485

<210> SEQ ID NO 19
<211> LENGTH: 158
<212> TYPE: DNA
<213> ORGANISM: Ixodes ricinus

<400> SEQUENCE: 19
caccagtgat gcttattgtt gcactgcact tgttgataat atccggtcgt cgaattgcac      60
ttcggaactt ccactccaac ttggcgagcc gtggattttg acttctcgtg atgctccacc     120
agacagttgc aggacttcag ctgcctagat ggagcctt                             158

<210> SEQ ID NO 20
<211> LENGTH: 146
<212> TYPE: DNA
<213> ORGANISM: Ixodes ricinus
<220> FEATURE:
<221> NAME/KEY: misc_feature
<222> LOCATION: (1)...(146)
<223> OTHER INFORMATION: n = A,T,C or G

<400> SEQUENCE: 20
ctgttgttga actgaaataa ataacaaaaa aatcataaag ntggaggaaa gatgatcgan      60
tccccgcccc ttgacaatcg tccgataaaa accaactata ttcngtcctt tttacaaaca     120
attccaantg tctgaccgaa ccgcga                                          146

<210> SEQ ID NO 21
<211> LENGTH: 140
<212> TYPE: DNA
<213> ORGANISM: Ixodes ricinus
<220> FEATURE:
<221> NAME/KEY: unsure
<222> LOCATION: (3)
<223> OTHER INFORMATION: A,C,T or G
<221> NAME/KEY: unsure
<222> LOCATION: (10)
<223> OTHER INFORMATION: A,C,T or G
<221> NAME/KEY: unsure
<222> LOCATION: (30)
<223> OTHER INFORMATION: A,C,T or G

<400> SEQUENCE: 21
ctnggacgan gtcctatgac ttgcgcttan gtttcttagt cttcttcggt ttcttctttt      60
tttgcttcgg tttttcggtg ggcgcaggtg tatagtcatc agtgtcggtg ggcccatccg     120
aatgagttgt caaatgacat                                                 140

<210> SEQ ID NO 22
<211> LENGTH: 143
<212> TYPE: DNA
<213> ORGANISM: Ixodes ricinus

<400> SEQUENCE: 22
tgccgaaaaa taacgatgat ttgacgttga ctctgcagaa gagtaaggtt ttcaccgaca      60
gttttctgtt tagcacgacg aaggataacg agcctatcga ttactacgtg agagccgaag     120
atgccgaacg agacatatat cac                                             143
```

-continued

```
<210> SEQ ID NO 23
<211> LENGTH: 140
<212> TYPE: DNA
<213> ORGANISM: Ixodes ricinus
<220> FEATURE:
<221> NAME/KEY: misc_feature
<222> LOCATION: (1)...(140)
<223> OTHER INFORMATION: n = A,T,C or G

<400> SEQUENCE: 23
tgttgctaca gactcgacgt ttcgagcttg ctcgccattt maagacaacg cactcacaga      60
atatttaagt gcgttcgtga wagctgtggg cttacgattg caggcgcttc antcaccagc     120
tgtgatatta magttcctag                                                 140

<210> SEQ ID NO 24
<211> LENGTH: 144
<212> TYPE: DNA
<213> ORGANISM: Ixodes ricinus

<400> SEQUENCE: 24
tcacgatagt tgaaacgttg aaacttgaaa tactcccaca gtcgttggat gcttcagaac      60
tgctaagaac ttcacacttt gcaagaagtw ccaaaatgaa agccgcgatg accgatgatt     120
tagcttccat cttctatcac ttga                                            144

<210> SEQ ID NO 25
<211> LENGTH: 95
<212> TYPE: DNA
<213> ORGANISM: Ixodes ricinus

<400> SEQUENCE: 25
gaccaccccg tccgaacttg ctaaakcaag caatggagtg aggtgttcta tgcgggttga      60
ttacaccaat ggcgctgcgt ggtgcgtggt gattt                                 95

<210> SEQ ID NO 26
<211> LENGTH: 1414
<212> TYPE: DNA
<213> ORGANISM: Ixodes ricinus
<220> FEATURE:
<221> NAME/KEY: CDS
<222> LOCATION: (143)..(1273)

<400> SEQUENCE: 26
gtagggccgt gcaagcgaag gcagcgaagg ctgcgagtgt acgtgcagtt cggaagtgca      60
atatcctgtt attaagctct aattagcaca ctgtgagtcg atcagaggcc tctcttaacg     120
ccacattgaa aaggatcca ag atg gag gca agt ctg agc aac cac atc ctt       172
                         Met Glu Ala Ser Leu Ser Asn His Ile Leu
                           1               5                  10 aac ttc tcc gtc gac cta tac aag cag ctg aaa ccc tcc ggc aaa gac       220
Asn Phe Ser Val Asp Leu Tyr Lys Gln Leu Lys Pro Ser Gly Lys Asp
             15                  20                  25 acg gca gga aac gtc ttc tgc tca cca ttc agt att gca gct gct ctg       268
Thr Ala Gly Asn Val Phe Cys Ser Pro Phe Ser Ile Ala Ala Ala Leu
         30                  35                  40 tcc atg gcc ctc gca gga gct aga ggc aac act gcc aag caa atc gct       316
Ser Met Ala Leu Ala Gly Ala Arg Gly Asn Thr Ala Lys Gln Ile Ala
     45                  50                  55 gcc atc ctg cac tca aac gac gac aag atc cac gac cac ttc tcc aac       364
Ala Ile Leu His Ser Asn Asp Asp Lys Ile His Asp His Phe Ser Asn
 60                  65                  70
```

-continued

| | |
|---|---|
| ttc ctt tgc aag ctt ccc agt tac gcc cca gat gtg gcc ctg cac atc<br>Phe Leu Cys Lys Leu Pro Ser Tyr Ala Pro Asp Val Ala Leu His Ile<br>75                   80                   85                   90 | 412 |
| gcc aat cgc atg tac tct gag cag acc ttc cat ccg aaa gcg gag tac<br>Ala Asn Arg Met Tyr Ser Glu Gln Thr Phe His Pro Lys Ala Glu Tyr<br>95                   100                  105 | 460 |
| aca acc ctg ttg caa aag tcc tac gac agc acc atc aag gct gtt gac<br>Thr Thr Leu Leu Gln Lys Ser Tyr Asp Ser Thr Ile Lys Ala Val Asp<br>110                   115                  120 | 508 |
| ttt gca gga aat gcc gac agg gtc cgt ctg gag gtc aat gcc tgg gtt<br>Phe Ala Gly Asn Ala Asp Arg Val Arg Leu Glu Val Asn Ala Trp Val<br>125                   130                  135 | 556 |
| gag gaa gtc acc agg tca aag atc agg gac ctg ctc gca cct gga act<br>Glu Glu Val Thr Arg Ser Lys Ile Arg Asp Leu Leu Ala Pro Gly Thr<br>140                   145                  150 | 604 |
| gtt gat tca tcg aca tca ctt ata tta gtg aat gcc att tac ttc aaa<br>Val Asp Ser Ser Thr Ser Leu Ile Leu Val Asn Ala Ile Tyr Phe Lys<br>155                   160                  165                  170 | 652 |
| ggt ctg tgg gat tct cag ttc aag cct agt gct acg aag ccg gga gat<br>Gly Leu Trp Asp Ser Gln Phe Lys Pro Ser Ala Thr Lys Pro Gly Asp<br>175                   180                  185 | 700 |
| ttt cac ttg aca cca cag acc tca aag aaa gtg gac atg atg cac cag<br>Phe His Leu Thr Pro Gln Thr Ser Lys Lys Val Asp Met Met His Gln<br>190                   195                  200 | 748 |
| gaa ggg gac ttc aag atg ggt cac tgc agc gac ctc aag gtc act gcg<br>Glu Gly Asp Phe Lys Met Gly His Cys Ser Asp Leu Lys Val Thr Ala<br>205                   210                  215 | 796 |
| ctt gag ata ccc tac aaa ggc aac aag acg tcg atg gtc att ctc ctg<br>Leu Glu Ile Pro Tyr Lys Gly Asn Lys Thr Ser Met Val Ile Leu Leu<br>220                   225                  230 | 844 |
| ccc gaa gat gta gag gga ctc tca gtc ctg gag gaa cac ttg acc gct<br>Pro Glu Asp Val Glu Gly Leu Ser Val Leu Glu Glu His Leu Thr Ala<br>235                   240                  245                  250 | 892 |
| ccg aaa ctg tcg gct ctg ctc ggc ggc atg tat gcg acg tcc gat gtc<br>Pro Lys Leu Ser Ala Leu Leu Gly Gly Met Tyr Ala Thr Ser Asp Val<br>255                   260                  265 | 940 |
| aac ttg cgc ttg ccg aag ttc aaa cta gag cag tcc ata ggt ttg aag<br>Asn Leu Arg Leu Pro Lys Phe Lys Leu Glu Gln Ser Ile Gly Leu Lys<br>270                   275                  280 | 988 |
| gat gta ctg atg gcg atg gga gtc aag gat ttc ttc acg tcc ctt gca<br>Asp Val Leu Met Ala Met Gly Val Lys Asp Phe Phe Thr Ser Leu Ala<br>285                   290                  295 | 1036 |
| gat ctt tct ggc atc agc gct gcg ggg aat ctg tgc gct tcg gat gtc<br>Asp Leu Ser Gly Ile Ser Ala Ala Gly Asn Leu Cys Ala Ser Asp Val<br>300                   305                  310 | 1084 |
| atc cac aag gct ttt gtg gaa gtt aat gag gag ggc aca gag gct gca<br>Ile His Lys Ala Phe Val Glu Val Asn Glu Glu Gly Thr Glu Ala Ala<br>315                   320                  325                  330 | 1132 |
| gct gcc act gcc ata ccc att atg ttg atg tgt gca aga ttt cca cag<br>Ala Ala Thr Ala Ile Pro Ile Met Leu Met Cys Ala Arg Phe Pro Gln<br>335                   340                  345 | 1180 |
| gtg gtg aac ttt ttc gtt gac cgc cca ttc atg ttc ttg atc cac agc<br>Val Val Asn Phe Phe Val Asp Arg Pro Phe Met Phe Leu Ile His Ser<br>350                   355                  360 | 1228 |
| cat gat cca gat gtt gtt ctc ttc atg gga tcc atc cgt gag ctc<br>His Asp Pro Asp Val Val Leu Phe Met Gly Ser Ile Arg Glu Leu<br>365                   370                  375 | 1273 |

-continued

```
taaaaagcat attcttaacg gcggccaatc agtctgtgga gttatctctt agtcactaat    1333
gtgtaacaat tctgcaatat tcagcttgtg tatttcagta acttgctaga tctttgtgtt    1393
gttgatgtta ggcttcttgc g                                              1414
```

<210> SEQ ID NO 27
<211> LENGTH: 377
<212> TYPE: PRT
<213> ORGANISM: Ixodes ricinus

<400> SEQUENCE: 27

```
Met Glu Ala Ser Leu Ser Asn His Ile Leu Asn Phe Ser Val Asp Leu
 1               5                  10                  15

Tyr Lys Gln Leu Lys Pro Ser Gly Lys Asp Thr Ala Gly Asn Val Phe
            20                  25                  30

Cys Ser Pro Phe Ser Ile Ala Ala Ala Leu Ser Met Ala Leu Ala Gly
        35                  40                  45

Ala Arg Gly Asn Thr Ala Lys Gln Ile Ala Ala Ile Leu His Ser Asn
    50                  55                  60

Asp Asp Lys Ile His Asp His Phe Ser Asn Phe Leu Cys Lys Leu Pro
65                  70                  75                  80

Ser Tyr Ala Pro Asp Val Ala Leu His Ile Ala Asn Arg Met Tyr Ser
                85                  90                  95

Glu Gln Thr Phe His Pro Lys Ala Glu Tyr Thr Thr Leu Leu Gln Lys
            100                 105                 110

Ser Tyr Asp Ser Thr Ile Lys Ala Val Asp Phe Ala Gly Asn Ala Asp
        115                 120                 125

Arg Val Arg Leu Glu Val Asn Ala Trp Val Glu Val Thr Arg Ser
    130                 135                 140

Lys Ile Arg Asp Leu Leu Ala Pro Gly Thr Val Asp Ser Ser Thr Ser
145                 150                 155                 160

Leu Ile Leu Val Asn Ala Ile Tyr Phe Lys Gly Leu Trp Asp Ser Gln
                165                 170                 175

Phe Lys Pro Ser Ala Thr Lys Pro Gly Asp Phe His Leu Thr Pro Gln
            180                 185                 190

Thr Ser Lys Lys Val Asp Met Met His Gln Glu Gly Asp Phe Lys Met
        195                 200                 205

Gly His Cys Ser Asp Leu Lys Val Thr Ala Leu Glu Ile Pro Tyr Lys
    210                 215                 220

Gly Asn Lys Thr Ser Met Val Ile Leu Leu Pro Glu Asp Val Glu Gly
225                 230                 235                 240

Leu Ser Val Leu Glu Glu His Leu Thr Ala Pro Lys Leu Ser Ala Leu
                245                 250                 255

Leu Gly Gly Met Tyr Ala Thr Ser Asp Val Asn Leu Arg Leu Pro Lys
            260                 265                 270

Phe Lys Leu Glu Gln Ser Ile Gly Leu Lys Asp Val Leu Met Ala Met
        275                 280                 285

Gly Val Lys Asp Phe Phe Thr Ser Leu Ala Asp Leu Ser Gly Ile Ser
    290                 295                 300

Ala Ala Gly Asn Leu Cys Ala Ser Asp Val Ile His Lys Ala Phe Val
305                 310                 315                 320

Glu Val Asn Glu Glu Gly Thr Glu Ala Ala Ala Thr Ala Ile Pro
                325                 330                 335

Ile Met Leu Met Cys Ala Arg Phe Pro Gln Val Val Asn Phe Val
            340                 345                 350
```

```
Asp Arg Pro Phe Met Phe Leu Ile His Ser His Asp Pro Asp Val Val
        355                 360                 365

Leu Phe Met Gly Ser Ile Arg Glu Leu
    370                 375

<210> SEQ ID NO 28
<211> LENGTH: 200
<212> TYPE: DNA
<213> ORGANISM: Ixodes ricinus

<400> SEQUENCE: 28
accgtaacca aaattgtttc tttccagaag aatggttcaa acttttcaaa cagatttcgg      60
aaactcttct tgcactttta aaatccaatc tacaatcttt cctcgcactt ctgaattgca     120
ttccagttta ccttccaagc aaacctcttt tggcaactcc agccgtactc catttcggca     180
taccacagtg catgcacttg                                                 200

<210> SEQ ID NO 29
<211> LENGTH: 241
<212> TYPE: DNA
<213> ORGANISM: Ixodes ricinus

<400> SEQUENCE: 29
cgtattcttt gaagatttgt atacgaaaca taaattcgtc atgcatactt ttgatggtta      60
cacgacatgc gaagctgccg acaaagaaga ctgggaagat aagaagcacc tagttacggt     120
agtgcgtgga ccggataaac gaaagtacac gtttctacgc aacattctca ccttacaacg     180
gagagtgaga gttagcaaaa caatgattga gctcgtacgg aacatgtcct gtaggacatt     240
t                                                                    241

<210> SEQ ID NO 30
<211> LENGTH: 313
<212> TYPE: DNA
<213> ORGANISM: Ixodes ricinus
<220> FEATURE:
<221> NAME/KEY: misc_feature
<222> LOCATION: (1)...(313)
<223> OTHER INFORMATION: n = A,T,C or G

<400> SEQUENCE: 30
aagcanccgg actacctgct tgaaaacgtt gtacgggcaa acttggacgg aaaactccca      60
gatgctactc cagttcctcc cggaagctac acgtacgctg agaatgataa cttcacctgc     120
tattccagaa gtacaccgtt tccggatggg gtgaatgttg tataacggct gctgggtgcg     180
gaagactatg atggattacg caaaaaagtt ctaaacgagt tgtttcccat cccggaaagt     240
ctgctgtatg ctgacatgat gcgacttgtg gctaagaaag acagagttga tcacactagt     300
ggatgacctg gga                                                       313

<210> SEQ ID NO 31
<211> LENGTH: 2417
<212> TYPE: DNA
<213> ORGANISM: Ixodes ricinus
<220> FEATURE:
<221> NAME/KEY: CDS
<222> LOCATION: (218)..(1492)

<400> SEQUENCE: 31
gtcgtagtcg tagtcgtagt cagttgcgca tgcgcgggc tttcctgtct ttcttgcctt       60
tctgcagtcg ttcaccaaca tgtggataca gctccggaga tttgtaaaca aatactgcac     120
```

-continued

```
ttttaagcaa gacttgatat ttagatcgat atcctcctgt tgtccgtctt gattaatcgg    180
ctctttaggg ttttttagaat aggcttttcg gtacgag atg ccc aaa gga aag agg    235
                                        Met Pro Lys Gly Lys Arg
                                          1               5 gga ccc aaa gca ggt ggc gcc gcg cgt ggt ggc cgg tgc gag gcc agc      283
Gly Pro Lys Ala Gly Gly Ala Arg Gly Gly Arg Cys Glu Ala Ser
             10                  15                  20 ctg gct ccg tcg tcc agc gac gag gag tcc aac gca gac acg gcg agc      331
Leu Ala Pro Ser Ser Ser Asp Glu Glu Ser Asn Ala Asp Thr Ala Ser
             25                  30                  35 gtg ctg agc tgc gcc tcg gag tct cgc tgt ggc agt gac ggc acc gtt      379
Val Leu Ser Cys Ala Ser Glu Ser Arg Cys Gly Ser Asp Gly Thr Val
         40                  45                  50 gga gac cca gaa gcg gag gag gct gtg ctg cat gac gac ttt gaa gac      427
Gly Asp Pro Glu Ala Glu Glu Ala Val Leu His Asp Asp Phe Glu Asp
 55                  60                  65                  70 aaa ctc aag gag gcc atc gac gga gct tcg cag aag agt gcc aaa gga      475
Lys Leu Lys Glu Ala Ile Asp Gly Ala Ser Gln Lys Ser Ala Lys Gly
             75                  80                  85 cgg ctg tcg tgc ctg gag gcg att cgc aag gcc ttt tcc acc aaa tac      523
Arg Leu Ser Cys Leu Glu Ala Ile Arg Lys Ala Phe Ser Thr Lys Tyr
             90                  95                 100 ctg tac gac ttc ctc atg gac aga ccg agc acg gtg tgc gac ctg gtg      571
Leu Tyr Asp Phe Leu Met Asp Arg Pro Ser Thr Val Cys Asp Leu Val
            105                 110                 115 gag cgt ggg gtg cgc aag ggc cga ggg gag gag gcg gcc ctg tgc gcc      619
Glu Arg Gly Val Arg Lys Gly Arg Gly Glu Glu Ala Ala Leu Cys Ala
        120                 125                 130 act ctc ggg gcc ctg gcc tgc gtc cag ctc ggg gtc ggg gcc gag gcg      667
Thr Leu Gly Ala Leu Ala Cys Val Gln Leu Gly Val Gly Ala Glu Ala
135                 140                 145                 150 gac gcc ctg ttc gac gcc ctg cgc cag ccg ctc tgc act ttg ctg ctt      715
Asp Ala Leu Phe Asp Ala Leu Arg Gln Pro Leu Cys Thr Leu Leu Leu
                155                 160                 165 gac ggg gcc cag ggg ccc tcc ccc agg gcc agg tgt gcc act gcc ctc      763
Asp Gly Ala Gln Gly Pro Ser Pro Arg Ala Arg Cys Ala Thr Ala Leu
            170                 175                 180 ggc ctc tgc tgc ttc gtg gtg gac tcg gac aac cag ctg gtg ctg cag      811
Gly Leu Cys Cys Phe Val Val Asp Ser Asp Asn Gln Leu Val Leu Gln
            185                 190                 195 ccg tgc atg gag gtg ctc tgg cag gtg gtg ggt gcc aag gcg ggc ccc      859
Pro Cys Met Glu Val Leu Trp Gln Val Val Gly Ala Lys Ala Gly Pro
200                 205                 210 ggc tct ccg gtg ctc cag gca gcg gcc ctg ctc gcc tgg ggc ctc ctg      907
Gly Ser Pro Val Leu Gln Ala Ala Ala Leu Leu Ala Trp Gly Leu Leu
215                 220                 225                 230 ctc agc gtg gct ccc gtc gac cgc ctg ctg gcg ctc acg cgc acg cac      955
Leu Ser Val Ala Pro Val Asp Arg Leu Leu Ala Leu Thr Arg Thr His
                235                 240                 245 ctg ccc cgg ctg cag gag ctg ctg gag agc ccc gac ctg gac ctg cgc      1003
Leu Pro Arg Leu Gln Glu Leu Leu Glu Ser Pro Asp Leu Asp Leu Arg
            250                 255                 260 att gcg gcc ggg gag gtg atc gcc gtc atg tac gag ggg gcc agg gac      1051
Ile Ala Ala Gly Glu Val Ile Ala Val Met Tyr Glu Gly Ala Arg Asp
            265                 270                 275 tac gac gag gac ttt gag gag ccc tcg gag tcc ctg tgt gcc cag ctg      1099
Tyr Asp Glu Asp Phe Glu Glu Pro Ser Glu Ser Leu Cys Ala Gln Leu
            280                 285                 290
```

| | | | | | | | | | | | | | | | |
|---|---|---|---|---|---|---|---|---|---|---|---|---|---|---|---|
| cgc | cag | ctg | gcc | acg | gac | agc | cag | aag | ttt | cgg | gcc | aag | aag | gag | cgg | 1147 |
| Arg | Gln | Leu | Ala | Thr | Asp | Ser | Gln | Lys | Phe | Arg | Ala | Lys | Lys | Glu | Arg | |
| 295 | | | | | 300 | | | | | 305 | | | | | 310 | |

```
cgc cag cag cgc tcc acc ttc agg gac gtc tac cgg gcc gtc agg gag   1195
Arg Gln Gln Arg Ser Thr Phe Arg Asp Val Tyr Arg Ala Val Arg Glu
                315                 320                 325 ggg gcc tct ccc gac gtg agc gtc aag ttt ggc cgg gaa gtc ctg gaa   1243
Gly Ala Ser Pro Asp Val Ser Val Lys Phe Gly Arg Glu Val Leu Glu
            330                 335                 340 ctg gac acc tgg agt cgc aag ctg cag tac gac gct ttc tgc cag ctg   1291
Leu Asp Thr Trp Ser Arg Lys Leu Gln Tyr Asp Ala Phe Cys Gln Leu
        345                 350                 355 ctg ggc tcc ggc atg aac ctg cac ctg gcc gtg aac gag ctg ctg agg   1339
Leu Gly Ser Gly Met Asn Leu His Leu Ala Val Asn Glu Leu Leu Arg
    360                 365                 370 gac atc ttt gaa ctg ggg cag gtg ctg gca acc gag gac cac att atc   1387
Asp Ile Phe Glu Leu Gly Gln Val Leu Ala Thr Glu Asp His Ile Ile
375                 380                 385                 390 tcc aag atc acc aag ttc gaa agg cac atg gtg aac atg gcc agc tgc   1435
Ser Lys Ile Thr Lys Phe Glu Arg His Met Val Asn Met Ala Ser Cys
                395                 400                 405 cgg gcc cgc acc aag aca cgc aac cgg ctg agg gac aag cgc gcc gac   1483
Arg Ala Arg Thr Lys Thr Arg Asn Arg Leu Arg Asp Lys Arg Ala Asp
            410                 415                 420 gtg gtc gcc tgaacctgcg gagggatgct tagctatgca ctcgccggcc           1532
Val Val Ala
        425
```

| | |
|---|---|
| taccctggcg ggactcgatg ccactcacga gtcggcgctc gcaaattcgc cgcccatcgt | 1592 |
| tacgcaatgg gagacaaagc tgcttttggc attaccgttt gaggtcggct ccaacccata | 1652 |
| gatgaatttc ttttttgtgg ccgtttctgg gttacatgtt ttgggggaag ggagtggaac | 1712 |
| tgtccggttc tttggcacac gtcaggttgc tcttgatgcg cgacgtgctt gtatttgggt | 1772 |
| actgccgaca ccaagcgttt cggcgattcc tggaaaagag tgcctctcgc tcgacgtttg | 1832 |
| gttgttttct gcgtggtccg tcgtcgacct tcgttcgtcc aaagacgccg tccggtttca | 1892 |
| tactcccccc cgcacacata tcgaggccaa ttaaattgct aagggtgccg ttgtcgtgca | 1952 |
| tctggcaggc tcagaagtgg cttatttgtc ttttaatttt gccgatgcac gcaaaaattg | 2012 |
| tcatttcttg aaagtttctc ttttattgcg tacacaattc aacttttatg taatttctga | 2072 |
| tggtctgttt tacgtgtgcg tgtgtaaaac gtaactttgg aagaattttt atgcacactg | 2132 |
| aacaaacgct cggtcctggg gttgaaagtg ctcggtgtgt gcatgagcta aagtgcaact | 2192 |
| gctttgttcc gaaggttttc tagtcgccga aatgtaccat tgtggacctt gttgcgagag | 2252 |
| accttggtct tctgggggag ctgctgtagc gtggcaagcc actattttgg gagcgacatt | 2312 |
| gcagagaaaa tcggcttttta gaaaggcacc tgcgcggcga gtggacgttt tttcgtatat | 2372 |
| actgcgaaaa aaaaaaaaaa aaaaaaaaaa aaaaaaaaaa aaaaa | 2417 |

<210> SEQ ID NO 32
<211> LENGTH: 425
<212> TYPE: PRT
<213> ORGANISM: Ixodes ricinus

<400> SEQUENCE: 32

Met Pro Lys Gly Lys Arg Gly Pro Lys Ala Gly Gly Ala Ala Arg Gly
1               5                   10                  15

Gly Arg Cys Glu Ala Ser Leu Ala Pro Ser Ser Asp Glu Glu Ser
            20                  25                  30

```
                                -continued

Asn Ala Asp Thr Ala Ser Val Leu Ser Cys Ala Ser Glu Ser Arg Cys
         35                  40                  45

Gly Ser Asp Gly Thr Val Gly Asp Pro Glu Ala Glu Glu Ala Val Leu
 50                  55                  60

His Asp Asp Phe Glu Asp Lys Leu Lys Glu Ala Ile Asp Gly Ala Ser
 65                  70                  75                  80

Gln Lys Ser Ala Lys Gly Arg Leu Ser Cys Leu Glu Ala Ile Arg Lys
                 85                  90                  95

Ala Phe Ser Thr Lys Tyr Leu Tyr Asp Phe Leu Met Asp Arg Pro Ser
            100                 105                 110

Thr Val Cys Asp Leu Val Glu Arg Gly Val Arg Lys Gly Arg Gly Glu
            115                 120                 125

Glu Ala Ala Leu Cys Ala Thr Leu Gly Ala Leu Ala Cys Val Gln Leu
130                 135                 140

Gly Val Gly Ala Glu Ala Asp Ala Leu Phe Asp Ala Leu Arg Gln Pro
145                 150                 155                 160

Leu Cys Thr Leu Leu Leu Asp Gly Ala Gln Gly Pro Ser Pro Arg Ala
                165                 170                 175

Arg Cys Ala Thr Ala Leu Gly Leu Cys Cys Phe Val Val Asp Ser Asp
            180                 185                 190

Asn Gln Leu Val Leu Gln Pro Cys Met Glu Val Leu Trp Gln Val Val
            195                 200                 205

Gly Ala Lys Ala Gly Pro Gly Ser Pro Val Leu Gln Ala Ala Ala Leu
210                 215                 220

Leu Ala Trp Gly Leu Leu Leu Ser Val Ala Pro Val Asp Arg Leu Leu
225                 230                 235                 240

Ala Leu Thr Arg Thr His Leu Pro Arg Leu Gln Glu Leu Leu Glu Ser
                245                 250                 255

Pro Asp Leu Asp Leu Arg Ile Ala Ala Gly Glu Val Ile Ala Val Met
            260                 265                 270

Tyr Glu Gly Ala Arg Asp Tyr Asp Glu Asp Phe Glu Glu Pro Ser Glu
            275                 280                 285

Ser Leu Cys Ala Gln Leu Arg Gln Leu Ala Thr Asp Ser Gln Lys Phe
290                 295                 300

Arg Ala Lys Lys Glu Arg Arg Gln Gln Arg Ser Thr Phe Arg Asp Val
305                 310                 315                 320

Tyr Arg Ala Val Arg Glu Gly Ala Ser Pro Asp Val Ser Val Lys Phe
                325                 330                 335

Gly Arg Glu Val Leu Glu Leu Asp Thr Trp Ser Arg Lys Leu Gln Tyr
            340                 345                 350

Asp Ala Phe Cys Gln Leu Leu Gly Ser Gly Met Asn Leu His Leu Ala
            355                 360                 365

Val Asn Glu Leu Leu Arg Asp Ile Phe Glu Leu Gly Gln Val Leu Ala
370                 375                 380

Thr Glu Asp His Ile Ile Ser Lys Ile Thr Lys Phe Glu Arg His Met
385                 390                 395                 400

Val Asn Met Ala Ser Cys Arg Ala Arg Thr Lys Thr Arg Asn Arg Leu
                405                 410                 415

Arg Asp Lys Arg Ala Asp Val Val Ala
            420                 425

<210> SEQ ID NO 33
<211> LENGTH: 933
<212> TYPE: DNA
```

<213> ORGANISM: Ixodes ricinus
<220> FEATURE:
<221> NAME/KEY: CDS
<222> LOCATION: (32)..(850)

<400> SEQUENCE: 33

```
gattgggaac ctcctattcc tcacttgaaa c atg gct gga ctc cgc tcc tgc       52
                                   Met Ala Gly Leu Arg Ser Cys
                                    1               5 atc ctc ctg gct ctt gcc act agt gcc ttc gcc ggt tac ctt cac ggt      100
Ile Leu Leu Ala Leu Ala Thr Ser Ala Phe Ala Gly Tyr Leu His Gly
         10                  15                  20 ggc ctt acc cac ggt gct ggg tac ggt tac ggt gtc ggc tac ggt tcc      148
Gly Leu Thr His Gly Ala Gly Tyr Gly Tyr Gly Val Gly Tyr Gly Ser
     25                  30                  35 ggc ctt ggc tat ggc ctt ggc tac ggt tcc ggc ctt ggc tat gga cat      196
Gly Leu Gly Tyr Gly Leu Gly Tyr Gly Ser Gly Leu Gly Tyr Gly His
 40                  45                  50                  55 gct gtt ggc ctt gga cac ggc ttt ggc tat tct ggt ctg acc ggc tac      244
Ala Val Gly Leu Gly His Gly Phe Gly Tyr Ser Gly Leu Thr Gly Tyr
                 60                  65                  70 agt gtg gct gcc cca gct agc tac gcc gtt gct gct cca gcc gtc agc      292
Ser Val Ala Ala Pro Ala Ser Tyr Ala Val Ala Ala Pro Ala Val Ser
             75                  80                  85 cgc acc gtt tcc act tac cac gct gct cca gct gtg gcc acc tac gcc      340
Arg Thr Val Ser Thr Tyr His Ala Ala Pro Ala Val Ala Thr Tyr Ala
         90                  95                 100 gct gct cct gtc gcc acc tat gct gtt gct cca gct gtc act agg gtt      388
Ala Ala Pro Val Ala Thr Tyr Ala Val Ala Pro Ala Val Thr Arg Val
     105                 110                 115 tcc ccc gtt cgc gcc gcc cca gct gtg gcc acg tac gcc gcc gct cca      436
Ser Pro Val Arg Ala Ala Pro Ala Val Ala Thr Tyr Ala Ala Ala Pro
120                 125                 130                 135 gtc gcc acc tac gcc gct gct cca gct gtg acc agg gtg tcc acc att      484
Val Ala Thr Tyr Ala Ala Ala Pro Ala Val Thr Arg Val Ser Thr Ile
                 140                 145                 150 cac gct gcc ccg gct gtg gcc aat tac gcc gtc gct cca gtc gcc acc      532
His Ala Ala Pro Ala Val Ala Asn Tyr Ala Val Ala Pro Val Ala Thr
             155                 160                 165 tat gcc gct gct cca gct gtg acc agg gtg tcc acc atc cac gcc gct      580
Tyr Ala Ala Ala Pro Ala Val Thr Arg Val Ser Thr Ile His Ala Ala
         170                 175                 180 cca gcc gtg gct agc tac cag acc tac cac gct cca gct gtc gcc act      628
Pro Ala Val Ala Ser Tyr Gln Thr Tyr His Ala Pro Ala Val Ala Thr
     185                 190                 195 gtg gct cat gct cca gct gtg gcc agc tac cag acc tac cac gct gcc      676
Val Ala His Ala Pro Ala Val Ala Ser Tyr Gln Thr Tyr His Ala Ala
200                 205                 210                 215 cca gcc gtg gct acc tac gcc cat gcc gct ccc gtc tac ggc tat ggt      724
Pro Ala Val Ala Thr Tyr Ala His Ala Ala Pro Val Tyr Gly Tyr Gly
                 220                 225                 230 gtc ggt acc ctc gga tat ggt gtc ggc cac tac ggc tac gga cac ggt      772
Val Gly Thr Leu Gly Tyr Gly Val Gly His Tyr Gly Tyr Gly His Gly
             235                 240                 245 ctt ggc agc tac ggc ctg aac tac ggt tac ggc ctc ggc acc tac ggt      820
Leu Gly Ser Tyr Gly Leu Asn Tyr Gly Tyr Gly Leu Gly Thr Tyr Gly
         250                 255                 260 gac tac acc acc ctt ctc cgc aag aag aag taaatggcac atctcaagag        870
Asp Tyr Thr Thr Leu Leu Arg Lys Lys Lys
     265                 270
```

-continued

```
agcccattgg actgccatcg acattcttct tcaataaaag agcccgaaga tggcattatt    930
ttt                                                                  933
```

<210> SEQ ID NO 34
<211> LENGTH: 273
<212> TYPE: PRT
<213> ORGANISM: Ixodes ricinus

<400> SEQUENCE: 34

```
Met Ala Gly Leu Arg Ser Cys Ile Leu Leu Ala Leu Thr Ser Ala
 1               5                  10                  15

Phe Ala Gly Tyr Leu His Gly Gly Leu Thr His Gly Ala Gly Tyr Gly
                20                  25                  30

Tyr Gly Val Gly Tyr Gly Ser Gly Leu Gly Tyr Gly Leu Gly Tyr Gly
                35                  40                  45

Ser Gly Leu Gly Tyr Gly His Ala Val Gly Leu Gly His Gly Phe Gly
                50                  55                  60

Tyr Ser Gly Leu Thr Gly Tyr Ser Val Ala Ala Pro Ala Ser Tyr Ala
 65                  70                  75                  80

Val Ala Ala Pro Ala Val Ser Arg Thr Val Ser Thr Tyr His Ala Ala
                85                  90                  95

Pro Ala Val Ala Thr Tyr Ala Ala Ala Pro Val Ala Thr Tyr Ala Val
                100                 105                 110

Ala Pro Ala Val Thr Arg Val Ser Pro Val Arg Ala Ala Pro Ala Val
                115                 120                 125

Ala Thr Tyr Ala Ala Ala Pro Val Ala Thr Tyr Ala Ala Ala Pro Ala
                130                 135                 140

Val Thr Arg Val Ser Thr Ile His Ala Ala Pro Ala Val Ala Asn Tyr
145                 150                 155                 160

Ala Val Ala Pro Val Ala Thr Tyr Ala Ala Pro Ala Val Thr Arg
                165                 170                 175

Val Ser Thr Ile His Ala Ala Pro Ala Val Ala Ser Tyr Gln Thr Tyr
                180                 185                 190

His Ala Pro Ala Val Ala Thr Val Ala His Ala Pro Ala Val Ala Ser
                195                 200                 205

Tyr Gln Thr Tyr His Ala Ala Pro Ala Val Ala Thr Tyr Ala His Ala
                210                 215                 220

Ala Pro Val Tyr Gly Tyr Gly Val Gly Thr Leu Gly Tyr Gly Val Gly
225                 230                 235                 240

His Tyr Gly Tyr Gly His Gly Leu Gly Ser Tyr Gly Leu Asn Tyr Gly
                245                 250                 255

Tyr Gly Leu Gly Thr Tyr Gly Asp Tyr Thr Thr Leu Leu Arg Lys Lys
                260                 265                 270

Lys
```

IDENTIFICATION AND MOLECULAR CHARACTERIZATION OF PROTEINS, EXPRESSED IN THE *IXODES RICINUS* SALIVARY GLANDS

CROSS REFERENCE TO RELATED APPLICATIONS

This application is a Continuation-in-Part of PCT Application Number PCT/BE00/00061 filed on Jun. 6, 2000, designating the United States of America and published in English on Dec. 21, 2000, the disclosure of which is incorporated herein by reference in its entirety. PCT/BE00/00061 claims priority to GB9913425.6, filed Jun. 9, 1999, the disclosure of which is incorporated herein by reference in its entirety.

FIELD OF THE INVENTION

The present invention is related to the molecular characterization of DNA sequences, which encode proteins expressed in the salivary glands of the *Ixodes ricinus* arthropod tick. These proteins are involved in the complex mechanism of interaction between this arthropod and its mammalian host. The invention relates to newly identified polynucleotides, polypeptides encoded by them and the use of such polynucleotides and polypeptides, and to their production.

BACKGROUND OF THE INVENTION

Ticks are hematophagous arthropods that feed on a wide diversity of hosts {Sauer, Annu. Rev. Entomol, 1995}. Unlike this group of arthropods, the Ixodid adult female ticks have the characteristics to ingest blood for an extended period of over 2 weeks.

Completion of the blood meal is dependent on the relationships of ticks with hosts species {Brossard Med. Vet. Entomol 1997}. Resistance to tick infestation implicates both innate and acquired immunity, and is characterized by reduced feeding, molting and mating capabilities that may lead to the death of the parasite. Acquired immunity of resistant hosts is mediated by a polarized Th1-type immune response, involving IFN-γ production and delayed type hypersensitivity reaction {Allen J R, Int. J. Parasitol. 1973}{Ganapamo, Immunol. 1995}.

Some hosts are unable to counteract the tick infestation {Ganapamo et al, 1995}. Indeed, during their blood meal, ticks circumvent host defences via pharmacologically active components secreted in their saliva. These factors can modulate both the innate and the acquired immunity of the host. In this way, the leukocyte responsiveness is modified during tick feeding {Ribeiro, Exp. Parasitol. 1987}{Kubes, Immunol. 1994}. For example, cytokines production is modulated, inducing a polarised Th2 immune response {Ganapamo, Immunol. 1996} {Kopecky, Parasite Immunol. 1998}.

Therefore, the complex tick-host molecular interaction can be considered as a balance between host defences raised against the parasite and the tick evasion strategies, facilitating feeding for an extended period. Although, there is extensive information about the effects of tick bioactive factors on host immune defences, little is known about the mechanisms of their actions. However, it has been observed that a wide range of new proteins is expressed during the blood meal {Wang, Parasitol. 1994}. Several of them might be essential for the completion of the tick feeding process.

SUMMARY OF THE INVENTION

The present invention is related to a new isolated and purified polynucleotide obtained from tick salivary gland and presenting more than 75% identity with at least one nucleotide sequence selected from the group consisting of SEQ.ID.NO.1, SEQ.ID.NO.2, SEQ.ID.NO.3, SEQ.ID.NO.4, SEQ.ID.NO.5, SEQ.ID.NO.6, SEQ.ID.NO.7, SEQ.ID.NO.9, SEQ.ID.NO.10, SEQ.ID.NO.11, SEQ.ID.NO.12, SEQ.ID.NO.13, SEQ.ID.NO.14, SEQ.ID.NO.15, SEQ.ID.NO.16, SEQ.ID.NO.17, SEQ.ID.NO.19, SEQ.ID.NO.20, SEQ.ID.NO.21, SEQ.ID.NO.22, SEQ.ID.NO.23, SEQ.ID.NO.24, SEQ.ID.NO.25, SEQ.ID.NO.26, SEQ.ID.NO.28, SEQ.ID.NO.29, SEQ.ID.NO.30, SEQ.ID.NO.31, SEQ.ID.NO.33 or a sequence complementary thereto, or a fragment thereof, as defined hereafter.

Preferably, the polynucleotide of claim 1, which presents at least 80% identity with at least one of said nucleotide sequences, more preferably at least 90% identity, more preferably with at least 95% identity, and even at least about 98 to 99% identity.

Preferably, the polynucleotide of claim 1, which presents at least 99% identity with at least one of said nucleotide sequences.

The present invention is also related to a polypeptide encoded by the polynucleotide of the present invention or a biologically active fragment or portion thereof.

Said polypeptide may be modified by or linked to at least one substitution group, preferably selected from the group consisting of amide, acetyl, phosphoryl, and/or glycosyl groups.

Moreover, said polypeptide may take the form of a "mature" protein.

It may also be part of a larger protein or part of a fusion protein.

Preferably, the polypeptide of the present invention further includes at least one additional amino acid sequence which contains secretory or leader sequences, prosequences, sequences which help in purification such as multiple histidine residues, or additional sequences for stability during production of recombinant molecules.

Another object of the present invention concerns a variant of the polynucleotide or the polypeptide of the present invention, a precise definition of this term being given hereafter.

Preferably, said variant varies from the referent by conservative amino acid substitutions.

Preferably, at least one residue is substituted in said variant with another residue of similar characteristics.

Advantageously, the substitutions in said variant are among Ala, Val, Leu and Ile; among Ser and Thr, among the acidic residues Asp and Glu; among Asn and Gln; among the basic residues Lys and Arg; or among aromatic residues Phe and Tyr.

Preferably, in the variant of the present invention, several amino acids are substituted, deleted or added in any combination.

Preferably, 5–10, more preferably 1–5, more preferably 1–2 amino acids are substituted, deleted or added in any combination, in said variant.

Said variant may be a naturally occurring allelic variant of an *Ixodes ricinus* salivary gland polypeptide present in *Ixodes ricinus* salivary glands.

The present invention is also related to a recombinant vector comprising at least one element selected from the polynucleotide, the polypeptide, and the variant of the present invention or fragments thereof.

Another object of the present invention concerns a cell transfected by or comprising the recombinant vector according to the invention.

The present invention further includes an inhibitor directed against said polynucleotide, polypeptide, or variant.

Said inhibitor is preferably an antibody or an hypervariable portion thereof.

The present invention is also related to an hybridoma cell line expressing said inhibitor.

Another object of the present invention concerns a pharmaceutical composition comprising an adequate pharmaceutical carrier and an element selected from the group consisting of said polynucleotide, polypeptide, variant, vector, cell, inhibitor or a mixture thereof.

Preferably, said pharmaceutical composition presents anti-coagulant properties and advantageously contains at least one polynucleotide selected from the group consisting of SEQ.ID.NO.7, SEQ.ID.NO.17, and SEQ.ID.NO.26, and fragments thereof or contains at least one polypeptide encoded by said polynucleotides or fragments thereof.

Preferably, the pharmaceutical composition presents immunomodulatory properties, and contains at least one polynucleotide selected from the group consisting of SEQ.ID.NO.12, SEQ.ID.NO.21, SEQ.ID.NO.26, and SEQ.ID.NO.31, and fragments thereof, or contains at least one polypeptide encoded by said polynucleotides or fragments thereof.

Another object of the invention is an immunological composition or vaccine for inducing an immunological response in a mammalian host to a tick salivary gland polypeptide which comprises at least one element of the group consisting of
a) a polynucleotide of tick salivary glands according to the invention;
b) a polypeptide of tick salivary glands according to the invention;
c) a variant according to the invention;
d) epitope-bearing fragments, analogs, outer-membrane vesicles or cells (attenuated or otherwise) of components a) or b) or c);
e) possibly a carrier.

The present invention is also related to a method for treating or preventing a disease affecting a mammal, said method comprising the step of administrating to said mammal a sufficient amount of the pharmaceutical composition or the immunological composition or vaccine according to the invention, in order to prevent or cure either the transmission of pathogenic agents by tick, especially by *Ixodes ricinus*, or the symptoms of diseases induced by tick or pathogenic agents transmitted by tick.

The present invention is also related to the use of the pharmaceutical composition or the immunological composition or vaccine according to the invention for the manufacture of a medicament in the treatment and/or prevention of diseases induced by tick or pathogenic agents transmitted by tick, especially by *Ixodes ricinus*.

Advantageously, said medicament may be used in transplantation, in rheumatology, but also in general treatment.

Finally, another object of the invention is a diagnostic kit for detecting a disease or susceptibility to a disease induced or transmitted by tick, especially *Ixodes ricinus*, which comprises:
a) at least one tick salivary gland polynucleotide of the invention, or a fragment thereof;
b) or at least one nucleotide sequence complementary to that of a);
c) or at least one tick salivary gland polypeptide, of the invention or a fragment thereof;
d) or at least one variant according to the invention or a fragment thereof
e) or an inhibitor of the invention;
f) or a phage displaying an antibody of the invention whereby a), b), c), d), e), f) may comprise a substantial component.

Definitions

Figure 1:
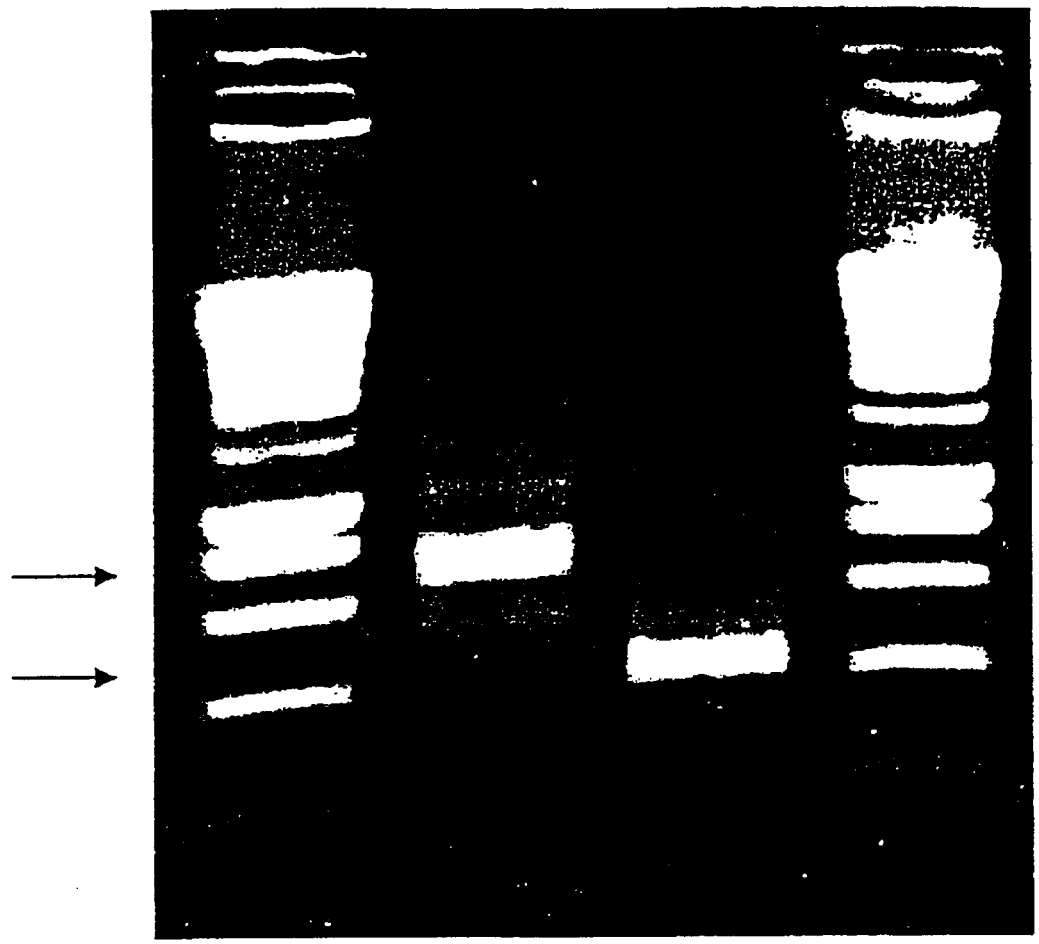
FIG. 1 presents results of RACE assay (Frohman et al., 1995) specific to SEQ.ID.NO.17 and SEQ.ID.NO.26. The reverse transcription step was carried out using 10 ng of mRNAs extracted from salivary gland of engorged ticks. The brightest bands represent the cDNA fragments corresponding to the 3' end of the targeted mRNA. The amplified products were subjected to agarose gel electrophoresis followed by staining the DNA fragments by ethidium bromide. Arrows indicate the position of the expected amplified products.

"Putative anticoagulant, anti-complementary and immunomodulatory" polypeptides refer to polypeptides having the amino acid sequence encoded by the genes indicated in the table. These present homologies with anticoagulant, anti-complementary and immunomodulatory polypeptides already existing in databases. These polypeptides belong to the Class I and Class II sequences (see table).

"Putative anticoagulant, anti-complementary and immunomodulatory" cDNAs refer to polynucleotides having the nucleotide sequence described in the table, or allele variants thereof and/or their complements. These present homologies with anticoagulant, anti-complementary and immunomodulatory polynucleotides already existing in databases. These cDNAs belong to the Class I and Class II sequences (see table)

Some polypeptide or polynucleotide sequences present low or no homologies with already existing polypeptides or polynucleotides in databases. These belong to the Class III (see table).

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslational natural processes or may be made by synthetic methods. Modifications include acetylation, acylation, ADP-ribosylation, amidation, covalent attachment of flavin, covalent attachment of a hem moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-linkings, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino of amino acids to proteins such as arginylation, and ubiquitination. See, for instance, PROTEINS—STRUCTURE AND MOLECULAR PROPERTIES, $2^{nd}$ Ed., T. E. Creighton, W. H. Freeman and Comany, New York, 1993 and Wolt, F., Posttranslational Protein Modifications : Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182 : 626–646 and Rattan et al, "Protein Synthesis : Posttranslational Modifications and Aging", *Ann NY Acad Sci* (1992) 663 48–62.

"Polynucleotide" generally refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. In addition, "Polynucleotide" refers to triple-stranded regions comprising RNA or DNA or both RNA and DNA. The term "Polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "Polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another reference polypeptide. Generally, differences are limited so that the sequences of the reference polypeptide and the variant are closely similar overall and, in many regions, identical. A variant and reference polypeptide may differ in amino acid sequence by one or more substitutions (preferably conservative), additions and deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis. Variants should retain one or more of the biological activities of the reference polypeptide. For instance, they should have similar antigenic or immunogenic activities as the reference polypeptide. Antigenicity can be tested using standard immunoblot experiments, preferably using polyclonal sera against the reference polypeptide. The immunogenicity can be tested by measuring antibody responses (using polyclonal sera generated against the variant polypeptide) against purified reference polypeptide in a standard ELISA test. Preferably, a variant would retain all of the above biological activities.

"Identity" is a measure of the identity of nucleotide sequences or amino acid sequences. In general, the sequences are aligned so that the highest order match is obtained. "Identify" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING : INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds, Humana Press, New Jersey, 1994; SEQUENCE ANALYSIS IN MOLECULAR BIOLOGY, von Heijne, G., Academic Press, 1987; and SEQUENCE ANALYSIS PRIMER, Gribskov, M. and Devereux, J., eds, M Stockton Press, New York, 1991). While there exist a number of methods to measure identity between two polynucleotide or polypeptide sequences, the term "identity" is well known to skilled artisans (Carillo, H., and Lipton, D., *SIAM J Applied Math* (1998) 48 : 1073). Methods commonly employed to determine identity or similarity between two sequences include, but are not limited to those disclosed in Guide to Huge Computers, Martin J. Bishop, ed., Academic Press, San Diego, 1994, and Carillo, H., and Lipton, D., *SIAM J Applied Math* (1988) 48 : 1073. Methods to determine identity and similarity are codified in computer programs. Preferred computer program methods to determine identity and similarity between two sequences include, but are not limited to, GCG program package (Devereux, J., et al., *J Molec Biol* (1990) 215 : 403). Most preferably, the program used to determine identity levels was the GAP program, as was used in the Examples hereafter.

As an illustration, by a polynucleotide having a nucleotide sequence having at least, for example, 95% "identity" to a reference nucleotide sequence is intended that the nucleotide sequence of the polynucleotide is identical to the reference sequence except that the polynucleotide sequence may include an average up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

Fragments of *I. ricinus* salivary gland polypeptides are also included in the present invention. A fragment is a polypeptide having an amino acid sequence that is the same as a part, but not all, of the amino acid sequence of the aforementioned *I. ricinus* salivary gland polypeptides. As with *I. ricinus* salivary gland polypeptides, fragment may be "free-standing" or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of the polypeptide. In this context "about" includes the particularly recited ranges larger or smaller by several, 5, 4, 3, 2 or 1 amino acid at either extreme or at both extremes.

Preferred fragments include, for example, truncated polypeptides having the amino acid sequence of the *I. ricinus* salivary gland polypeptides, except for deletion of a continuous series of residues that includes the amino terminus, or a continuous series of residues that includes the carboxyl terminus and/or transmembrane region or deletion of two continuous series of residues, one including the amino terminus and one including the carboxyl terminus. Also preferred are fragments characterised by structural or functional attributes such as fragments that comprise alpha-helix and alpha-helix forming regions, beta-sheet and beta-sheet forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate *I. ricinus* salivary gland protein activity, including those with a similar activity or an improved activity, or with a decreased undesirable activity. Also included are those that are antigenic or immunogenic in an animal or in a human.

EXAMPLES

Example 1

Characterization of the Induced Genes

Genes are induced in the salivary glands of *Ixodes ricinus* during the slow-feeding phase of the blood meal. The cloning of these genes was carried out by setting up two complementary DNA (cDNA) libraries. The first one is a subtractive library based on the methodology described by Lisitsyn et al. (*Science* 259, 946–951,1993) and improved by Diatchenko et al. (*Proc. Natl. Acad. Sci. USA* 93, 6025–6030, 1996). This library cloned selectively induced mRNA during the tick feeding phase. The second library is a full-length cDNA library, which was constructed by using the basic property of mRNAs (presence of a polyA tail in its 3' end and a cap structure in its 5' end). This cDNA library permitted the cloning of full-length cDNAs, corresponding to some incomplete cDNA sequences identified in the subtractive cDNA library.

The subtractive library was set up by subtracting uninduced-cDNAs (synthesized from mRNAs equally expressed in the salivary glands of both unfed and engorged ticks) from induced-cDNAs (synthesised from mRNAs differentially expressed in the salivary gland at the end of the slow-feeding phase). The induced-cDNAs was digested by a restriction enzyme, divided into two aliquots, and distinctively modified by the addition of specific adapters. As for the induced-cDNAs, the uninduced cDNAs was also digested by the same restriction enzyme and then mixed in excess to each aliquot of modified induced-cDNA. Each mixture of uninduced-/induced-cDNAs was subjected to a denaturation step, immediately followed by an hybridisation step, leading to a capture of homologous induced-cDNAs by the uninduced-cDNA. Each mixture was then mixed together and subjected again to a new denaturation/ hybridisation cycle. Among the hybridised cDNA molecules, the final mixture comprises induced-cDNAs with different adapters at their 5' and 3' end. These relevant cDNAs were amplified by polymerase chain reaction (PCR), using primers specific to each adapter located at each end of the cDNA molecules. The PCR products were then ligated into the pCRII™ vector by A-T cloning and cloned in an TOP-10 E. coli strain. The heterogeneity of this subtractive library was evaluated by sequencing 96 randomly chosen recombinant clones. The "induced" property of these cDNA sequences was checked by reverse transcription-PCR (RT-PCR) on mRNA extracted from salivary glands of engorged and unfed ticks. Finally, the full-length induced-cDNA was obtained by screening the full-length cDNA library using, as a probe, some incomplete induced-cDNAs isolated from the subtractive library. These full-length induced DNA molecules were sequenced and compared to known polypeptide and polynucleotide sequences existing in the EMBL/ GenBank databases.

The full-length cDNA library was set up by using the strategy developed in the "CapFinder PCR cDNA Library Construction Kit" (Clontech). This library construction kit utilises the unique CapSwitch™ oligonucleotide (patent pending) in the first-strand synthesis, followed by a long-distance PCR amplification to generate high yields of full-length, double-stranded cDNAs. All commonly used cDNA synthesis methods rely on the ability of reverse transcriptase to transcribe mRNA into single stranded DNA in the first-strand reaction. However, because the reverse transcriptase cannot always transcribe the entire mRNA sequence, the 5' ends of genes tend to be under-represented in cDNA population. This is particularly true for long mRNAs, especially if the first-strand synthesis is primed with oligo(dT) primers only, or if the mRNA has a persistent secondary structure. Furthermore, the use of T4 DNA polymerase to generate blunt cDNA ends after second-strand synthesis commonly results in heterogeneous 5' ends that are 5–30 nucleotides shorter than the original mRNA (D'Alessio, 1988). In the CapFinder cDNA synthesis method, a modified oligo(dT) primer is used to prime the first-strand reaction, and the CapSwitch oligonucleotide acts as a short, extended template at the 5' end for the reverse transcriptase. When the reverse transcriptase reaches the 5' end of the mRNA, the enzyme switches templates and continues replicating to the end of the CapSwitch oligonucleotide. This switching in most cases occurs at the 7-methylguanosine cap structure, which is present at the 5' end of all eukaryotic mRNAs (Furuichi & Miura, 1975). The resulting full-length single stranded cDNA contains the complete 5' end of the mRNA as well as the sequence complementary to the CapSwitch oligonucleotide, which then serves as a universal PCR priming site (CapSwitch anchor) in the subsequent amplification. The CapSwitch-anchored single stranded cDNA is used directly (without an intervening purification step) for PCR. Only those oligo(dT)-primed single stranded cDNAs having a CapSwitch anchor sequence at the 5' end can serve as templates and be exponentially amplified using the 3' and 5' PCR primers. In most cases, incomplete cDNAs and cDNA transcribed from poly-A RNA will not be recognised by the CapSwitch anchor and therefore will not be amplified.

At the end of these reactions, the full-length cDNA PCR products was ligated into the pCRII cloning vector (Invitrogen) and used for the transformation of XL2 E. coli strain. The full-length cDNA library was then screened by using, as a probe, the incomplete induced-cDNAs isolated from the subtractive library.

Ninety-six clones of subtractive library were randomly sequenced, and their DNA and amino acid translated sequences were compared to DNA and protein present in databases. Among these, 27 distinct family sequences were identified, and 3 of them were selected for further characterization of their corresponding full-length mRNA sequence. These 3 sequences matched the sequence of i) the human tissue factor pathway inhibitor (TFPI), ii) the human thrombin inhibitor gene, and iii) a snake venom zinc-dependent metalloprotease protein. These genes encode proteins that could be involved in the inhibition of the blood coagulation. The other 24 family sequences presented low or no homologies with polynucleotide and polypeptide sequences existing in databases. Screening of the full-length cDNA library using oligonucleotide probes specific to the 3 previously selected subtractive clones lead to the recovery of the corresponding full-length cDNAs. Random screening of this library led to the selection of 2 other clones. One is closely homologous to an interferon-like protein, whereas the other shows homologies to the *Streptococcus equi* M protein, an anti-complement protein.

These polypeptides expressed by *I. ricinus* salivary glands include the polypeptides encoded by the cDNAs defined in the tables, and polypeptides comprising the amino acid sequences which have at least 75% identity to that encoded by the cDNAs defined in the tables over their complete length, and preferable at least 80% identity, and more preferably at least 90% identity. Those with about 95–99% are highly preferred.

The *I. ricinus* salivary gland polypeptides may be in the form of the "mature" protein or may be a part of a larger protein such as a fusion protein. It may be advantageous to include an additional amino acid sequence, which contains secretory or leader sequences, pro-sequences, sequences which help in purification such as multiple histidine residues, or an additional sequence for stability during recombinant production.

Preferably, all of these polypeptide fragments retain parts of the biological activity (for instance antigenic or immunogenic) of the *I. ricinus* salivary gland polypeptides, including antigenic activity. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination. Most preferred variants are naturally occurring allelic variants of the *I. ricinus* salivary gland polypeptide present in *I. ricinus* salivary glands.

The *I. ricinus* salivary gland polypeptides of the invention can be prepared in any suitable manner. Such polypeptides include isolated naturally occurring polypeptides, recombinant polypeptides, synthetic polypeptides, or polypeptides produced by a combination of these methods. Means for preparing such polypeptides are well understood in the art.

The *I. ricinus* salivary gland cDNAs (polynucleotides) include isolated polynucleotides which encode *I. ricinus* salivary gland polypeptides and fragments thereof, and polynucleotides closely related thereto. More specifically, *I. ricinus* salivary gland cDNAs of the invention include a polynucleotide comprising the nucleotide sequence of cDNAs defined in the table, encoding a *I. ricinus* salivary gland polypeptide. The *I. ricinus* salivary gland cDNAs further include a polynucleotide sequence that has at least 75% identity over its entire length to a nucleotide sequence encoding the *I. ricinus* salivary gland polypeptide encoded by the cDNAs defined in the tables, and a polynucleotide comprising a nucleotide sequence that is at least 75% identical to that of the cDNAs defined in the tables, in this regard, polynucleotides at least 80% identical are particularly preferred, and those with at least 90% are especially preferred. Furthermore, those with at least 95% are highly preferred and those with at least 98–99% are most highly preferred, with at least 99% being the most preferred. Also included under *I. ricinus* salivary gland cDNAs is a nucleotide sequence, which has sufficient identity to a nucleotide sequence of a cDNA defined in the tables to hybridise under conditions usable for amplification or for use as a probe or marker. The invention also provides polynucleotides which are complementary to such *I. ricinus* salivary gland cDNAs.

These nucleotide sequences defined in the tables as a result of the redundancy (degeneracy) of the genetic code may also encode the polypeptides encoded by the genes defined in the tables.

When the polynucleotides of the invention are used for the production of an *I. ricinus* salivary gland recombinant polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro-or preproprotein sequence, or other fusion peptide portions. For example, a marker sequence, which facilitates purification of the fused polypeptide can be encoded. Preferably, the marker sequence is a hexa-histidine peptide, as provided in the pQE vector (Qiagen, Inc.) and described in Gentz et al, *Proc Natl Acad Sci USA* (1989) 86:821–824, or is an HA tag, or is glutathione-s-transferase. The polynucleotide may also contain non-coding 5' and 3' sequences, such as transcribed, non-translated sequences, splicing and polyadenylation signals, ribosome binding sites and sequences that stabilize mRNA.

Further preferred embodiments are polynucleotides encoding *I. ricinus* salivary gland protein variants comprising the amino acid sequence of the *I. ricinus* salivary gland polypeptide encoded by the cDNAs defined by the table respectively in which several, 10–25, 5–10, 1–5, 1–3, 1–2 or 1 amino acid residues are substituted, deleted or added, in any combination. Most preferred variant polynucleotides are those naturally occurring *I. ricinus* sequences that encode allelic variants of the *I. ricinus* salivary gland proteins in *I. ricinus*.

The present invention further relates to polynucleotides that hybridise preferably stringent conditions to the herein above-described sequences. As herein used, the term "stringent conditions" means hybridisation will occur only if there is at least 80%, and preferably at least 90%, and more preferably at least 95%, yet even more preferably 97–99% identity between the sequences.

Polynucleotides of the invention, which are identical or sufficiently identical to a nucleotide sequence of any gene defined in the table or a fragment thereof, may be used as hybridisation probes for cDNA clones encoding *I. ricinus* salivary gland polypeptides respectively and to isolate cDNA clones of other genes (including cDNAs encoding homologs and orthologs from species other than *I. ricinus*) that have a high sequence similarity to the *I. ricinus* salivary gland cDNAs. Such hybridisation techniques are known to those of skill in the art. Typically these nucleotide sequences are 80% identical, preferably 90% identical, more preferably 95% identical to that of the referent. The probes generally comprise at least 15 nucleotides, preferably, at least 30 nucleotides or at least 50 nucleotides. Particularly preferred probes range between 30 and 50 nucleotides. In one embodiment, to obtain a polynucleotide encoding *I. ricinus* salivary gland polypeptide, including homologues and orthologues from species other than *I. ricinus*, comprises the steps of screening an appropriate library under stringent hybridisation conditions with a labelled probe having a nucleotide sequence contained in one of the gene sequences defined by the table, or a fragment thereof; and isolating full-length cDNA clones containing said polynucleotide sequence. Thus in another aspect, *I. ricinus* salivary gland polynucleotides of the present invention further include a nucleotide sequence comprising a nucleotide sequence that hybridise under stringent condition to a nucleotide sequence having a nucleotide sequence contained in the cDNAs defined in the tables or a fragment thereof. Also included with *I. ricinus* salivary gland polypeptides are polypeptides comprising amino acid sequences encoded by nucleotide sequences obtained by the above hybridisation conditions (conditions under overnight incubation at 42° C. in a solution comprising: 50% formamide, 5×SSC (150 mM NaCl, 15 mM trisodium citrate), 50 mM sodium phosphate (pH 7.6), 5× Denhardt's solution, 10% dextran sulfate, and 20 microgram/ml denatured, sheared salmon sperm DNA, followed by washing the filters in 0.1×SSC at about 65° C.).

The polynucleotides and polypeptides of the present invention may be employed as research reagents and materials for the development of treatments and diagnostics tools specific to animal and human disease.

This invention also relates to the use of *I. ricinus* salivary gland polypeptides, or *I. ricinus* salivary gland polynucleotides, for use as diagnostic reagents.

Materials for diagnosis may be obtained from a subject's cells, such as from blood, urine, saliva, tissue biopsy.

Thus in another aspect, the present invention relates to a diagnostic kit for a disease or susceptibility to a disease which comprises:

(a) an *I. ricinus* salivary gland polynucleotide, preferably the nucleotide sequence of one of the gene sequences defined by the table, or a fragment thereof;
(b) a nucleotide sequence complementary to that of (a);
(c) an *I. ricinus* salivary gland polypeptide, preferably the polypeptide encoded by one of the gene sequences defined in the table, or a fragment thereof;
(d) an antibody to an *I. ricinus* salivary gland polypeptide, preferably to the polypeptide encoded by one of the gene sequences defined in the table; or
(e) a phage displaying an antibody to an *I. ricinus* salivary gland polypeptide, preferably to the polypeptide encoded by one of the cDNAs sequences defined in the table.

It will be appreciated that in any such kit, (a), (b), (c), (d) or (e) may comprise a substantial component.

Another aspect of the invention relates to a method for inducing an immunological response in a mammal which comprises inoculating the mammal with *I. ricinus* salivary gland polypeptide or epitope-bearing fragments, analogues, outer-membrane vesicles or cells (attenuated or otherwise), adequate to produce antibody and/or T cell immune response to protect said animal from bacteria and viruses which could be transmitted during the blood meal of *I. ricinus* and related species. In particular the invention relates to the use of *I. ricinus* salivary gland polypeptides encoded by the cDNAs defined in the tables. Yet another aspect of the invention relates to a method of inducing immunological response in a mammal which comprises, delivering *I. ricinus* salivary gland polypeptide via a recombinant vector directing expression of *I. ricinus* salivary gland polynucleotide in vivo in order to induce such an immunological response to produce antibody to protect said animal from diseases transmitted by *I. ricinus* ticks or other related species (Lyme disease, tick encephalitis virus disease, . . . ).

A further aspect of the invention relates to an immunological composition or vaccine formulation which, when introduced into a mammalian host, induces an immunological response in that mammal to a *I. ricinus* salivary gland polypeptide wherein the composition comprises a *I. ricinus* salivary gland cDNA, or *I. ricinus* salivary gland polypeptide or epitope-bearing fragments, analogs, outer-membrane vesicles or cells (attenuated or otherwise). The vaccine formulation may further comprise a suitable carrier. The *I. ricinus* salivary gland polypeptide vaccine composition is preferably administered orally or parenterally (including subcutaneous, intramuscular, intravenous, intradermal injection). Formulations suitable for parenteral administration include aqueous and non-aqueous sterile injection solutions which may contain anti-oxidants, buffers, bacteriostats and solutes which render the formulation iotonic with the blood of the recipient; and aqueous and non-aqueous sterile suspensions which may include suspending agents or thickening agents. The formulations may be presented in unit-dose or multi-dose containers, for example; sealed ampoules and vials and may be stored in a freeze-dried condition requiring only the addition of the sterile liquid carrier immediately prior to use. The vaccine formulation may also include adjuvant systems for enhancing the immunogenicity to the formulation, such as oil-in water systems and other systems known in the art. The dosage will depend on the specific activity of the vaccine and can be readily determined by routine experimentation.

Yet another aspect relates to an immunological/vaccine formulation which comprises the polynucleotide of the invention. Such techniques are known in the art, see for example Wolff et al, *Sciences*, (1990) 247 1465–8.

Another aspect of the invention related to the use of these *I. ricinus* salivary gland polypeptides as therapeutic agents. In considering the particular potential therapeutic areas for such products, the fields covered by these products are: haematology (particularly coagulation clinics), transplantation (for immunosuppression control), rheumatology (for anti-inflammatories), and general treatment (for specific or improved anaesthetics).

TABLE 1

Sequences identified in the subtractive and the cDNA full-length libraries

| | Motifs | Similar sequences in databases | Score | Class |
|---|---|---|---|---|
| Seq.1 | | No significative identity | | III |
| Seq.2 | | No significative identity | | III |
| Seq.3 | | No significative identity | | III |
| Seq.4 | | No significative identity | | III |
| Seq.5 | Prokaryotic mbre lipoprotein lipid attachment site | No significative identity | | III |
| Seq.6 | | *R. melioti* Nitrogen fixation (fixF) | 0.00089 | III |
| | | Human Apolipoprotein B-100 | 0.0045 | III |
| | | Hu.mRNA for cAMP response element (CRE-BP1) binding prot | 0.057 | III |
| Seq.7 | Kunitz family of serine protease inhibitor | Human BAC clone GS345D13 | $4, 7^{13}$ | I |
| | | *H. sap* Tissue factor Pathway Inhibitor PRESENT INVENTION-2 | $4^{-12}$ | I |
| Seq.9 | Prokaryotic mbrne lipoprotein lipid attachment site | No significative identity | | III |
| Seq.10 | | Pea mRNA for GTP binding protection. | 0.48 | III |
| Seq.11 | | No significative identity | | III |
| Seq.12 | | IL-11 R-Beta gene | 0.18 | II |
| Seq.13 | | No significative identity | | III |
| Seq.14 | | *C. gloeosporioides* cutinase gene | 0.082 | III |
| Seq.15 | | No significative identity | | III |
| Seq.16 | | Mouse Mrna for secretory protection cont. thranspondine motifs | 0.014 | III |
| Seq.17 | Zinc dependent metallopeptidase family | *B. jararaca* mRNA for jararhagin | $1, 1^{-5}$ | I |
| | | *Agkistrodon contortrix* metalloproteinase precursor | $3, 9^{-5}$ | I |
| Seq.19 | | *O. aries* gene for ovine INFRINGEMENT-alpha | 0.7 | II |
| | | | 0.88 | II |
| | | Interferon-omega 45 | 0.89 | II |
| | | Interferon-omega 20 | 0.85 | III |
| | | RCPT PGE2 PGE Rcpt EP2 | 0.85 | III |
| Seq.20 | | No significative identity | | III |
| Seq.21 | | IgG1L chain directed against human IL2 rcpt Tac protection | 0.19 | II |
| | | Var region of light chain of MAK447/179 | 0.2 | II |

TABLE 1-continued

Sequences identified in the subtractive and the cDNA full-length libraries

| | Motifs | Similar sequences in databases | Score | Class |
|---|---|---|---|---|
| Seq.22 | | No significative identity | | III |
| Seq.23 | | No significative identity | | III |
| Seq.24 | | *Mus Musculus* neuroactin | 0.42 | III |
| Seq.25 | | No significative identity | | III |
| Seq.26 | | *H. sapiens* thrombin inhibitor | 2, $1^{-12}$ | I |
| | | Cycloplasmic antiproteinase 38kDa intracellular serine protection. | 2, $3^{-12}$ | I |
| Seq.28 | | No significative identity | | III |
| Seq.29 | | No significative identity | | III |
| Seq.30 | | *Mus musculus* transcription factor ELF3 (fasta) | 0.053 | III |
| Seq.31 28 | | *Homo sapiens* putative interferon-related protein (SM15) mRNA | 1.70E-22 | II |
| Seq.33 | | *R. norvegicus* Mrna for leucocyle common antigen-related protein | 4.80E-09 | II |

(SEQ. ID. NO. 26 (Iris): homology with *H. sapiens* thrombin inhibitor 2.1-12, class I
Class I: putative anticoagulant homologs; Class II: putative immunomodulatory homologs; Class III: low or no homologies found in the databases).

TABLE 2

Biological characteristics of the selected clones

| Clone | Full-length sequences similarly to databases | Fasta/Blastp Scores[a] | ORF (aa) | Motifs | Signal peptide scores[b] | Sp length/ Prob. | Nucleotide in position $-3^c$ |
|---|---|---|---|---|---|---|---|
| Seq31 | *Homo sapiens* putative interferon-related gene (SKMc15) [U09585] | $1,8.10^{-36}/1.10^{-71}$ | 426 | | D 5,4/F[e] | 48aa/8, $4.10^{-1}$ | G |
| Seq33 | *R. norvegicus* leukocyte common antigen (LAR) mRNA [X83546] | $7,8.10^{-11}$/N | 274 | | 10,2/S | 18aa/7, $4.10^{-3}$ | A |
| Seq17 | Mouse mRNA for secretory protein containing thrombospondin motives [D67076] | $0,002/6.10^{-7}$ | 489 | Metallo pep-tidase | 7,9/S | 19aa/7, $4.10^{-4}$ | G |
| Seq26 | Pig leukocyte elastase inhibitor mRNA [P80229] | $0/7.10^{-67}$ | 378 | Serpin | 8,5/S | 51aa/3, $28.10^{-3}$ | A |
| Seq7 | Human Tissue Factor Pathway Inhibitor [P48307] | $4,8.10^{-12}/2.10^{-5}$ | 87 | Kunitz | 6,5/S | 19aa:1, $8.10^{-4}$ | G |

[a]No score (N)
[b]Succeeded (S) and Failed (F)
[c]Guanine (G) and Adenine (A)
[d]von Heijne analysis
[e]McGeoch analysis Example 2

Construction of a Representational Difference Analysis (RDA) Subtractive Library The salivary glands of 5 day engorged or unfed free of pathogen *I. ricinus* female adult ticks were used in this work.

When removed, these glands were immediately frozen in liquid nitrogen and stored at −80° C. To extract RNA messengers (mRNA), the salivary glands were crushed in liquid nitrogen using a mortar and a pestle. The mRNAs were purified by using an oligo-dT cellulose (Fast Track 2.0 kit, Invitrogen, Groningen, The Netherlands). Two micrograms of mRNAs were extracted from 200 salivary glands of fed ticks, and 1.5 μg of mRNAs were also extracted from 1,000 salivary glands of unfed ticks.

All procedures were performed as described by Hubank and Schatz (1994). Double-stranded cDNAs were synthesised using the Superscript Choice System (Life Technologies, Rockville, Md. USA). The cDNAs were digested with DpnII restriction enzyme, ligated to R-linkers, amplified with R-24 primers (Hubank and Schatz, 1994), and finally digested again with the same enzyme to generate a "tester" pool consisting of cDNAs from salivary glands of fed ticks and a "driver" pool consisting of cDNAs from salivary glands of unfed ticks. The first round of the subtractive hybridisation process used a tester/driver ratio of 1:100. The second and third rounds utilised a ratio of 1:400 and 1:200,000, respectively. After three cycles of subtraction and amplification, the DpnII-digested differential products were subdivided according to size into 4 different fractions on a 1.7% electrophoresis agarose gel, and subcloned the BamHI site of the pTZ19r cloning vector. The ligated product was used to transform TOP-10 E. coli competent cells (Invitrogen, Groningen, The Nederlands). Nine thousand six hundred clones of this subtractive library were randomly selected, and individually put in 96-well microplates and stored at −80° C. This subtractive library was analysed by sequencing 89 randomly chosen clones, using M13 forward and reverse primers specific to a region located in the pT19r cloning vector. The DNA sequences of these 89 clones were compared, and 27 distinct family sequences were identified. Homology of these sequences to sequences existing in databases is presented in Table 1.

The subtractive sequences 1 to 27 are presented in the sequence-listing file (except for sequences 17 and 26 whose complete mRNA sequences are presented; see also Example 2). Three sequences (SEQ.ID.NO.7, 17 and 26) were selected for further characterization of their corresponding full-length mRNA sequence. These 3 sequences matched the sequence of i) the human tissue factor pathway inhibitor (TFPI), ii) a snake venom zinc dependent metallopeptidase protein, and iii) the human thrombin inhibitor protein, corresponding to SEQ.ID.NO.7, 17 and 26, respectively. These genes encode proteins which could be involved in the inhibition of the blood coagulation or in the modulation of the host immune response.

Example 3

Construction of the Full Length cDNA Library and Recovery of Full Length cDNAs Sequences by Screening of This Full Length cDNA Library This library was set up using mRNAs extracted from salivary glands of engorged ticks. The mRNAs (80 ng) were subjected to reverse transcription using a degenerated oligo-dT primer (5'A(T)30VN-3'), the Smart™ oligonucleotide (Clontech, Palo Alto, USA), and the Superscript II reverse transcriptase (Life Technologies, Rockville, Md., USA). The single strand cDNA mixture was used as template in a hot start PCR assay including the LA Taq polymerase (Takara, Shiga, Japan), the modified oligo-dT primer and a 3'-Smart primer specific to a region located at the 5' end of the Smart™ oligonucleotide. The PCR protocol applied was: 1 min at 95° C., followed by 25 sec at 95° C./5 min at 68° C., 25 times; and 10 min at 72° C. The amplified double stranded cDNA mixture was purified with a Centricon 30 concentrator (Millipore, Bedford, USA). The cDNAs were divided into 4 fractions ranging from 0.3 to 0.6 kb, 0.6 to 1 kb, 1 kb to 2 kb, and 2 kb to 4 kb on a 0,8% high grade agarose electrophoresis gel. Each fraction was recovered separately by using the Qiaex II extraction kit (Qiagen, Hilden, Germany). The 4 fractions were ligated individually into the pCRII cloning vector included in the TOPO cloning kit (Invitrogen, Groningen, The Netherlands). The ligated fractions were then used to transform XL2-Blue ultracompetent E. coli cells (Stratagene, Heidelburg, Germany). The resulted recombinant clones were stored individually in microplates at −80° C. Ten clones were randomly chosen for partial or complete sequencing. As a result of this procedure, 2 cDNA sequences (SEQ.ID.NO.31 and SEQ.ID.NO.33, see Table 1) were selected for their homology to sequence databases. One is closely homologous to an interferon-like protein (SEQ.ID.NO.31), whereas the other shows homologies to the Rattus norvegicus leukocyte common antigen-related protein (SEQ.ID.NO.33).

The 4 different fractions of the full-length cDNA library were screened with radio-labelled oligonucleotide probes specific to selected clones identified in the subtractive cDNA library. The labelling of these oligo probes was performed as described in "Current Protocols in Molecular Biology" (Ausubel et al, 1995, J. Wiley and sons, Eds). These 4 different fractions were then plated on nitrocellulose membranes and grown overnight at 37° C. These membranes were denatured in NaOH 0.2M/NaCl 1.5M, neutralised in Tris 0.5M pH 7.5—NaCl 1.5M and fixed in 2× SSC (NaCl 0.3 M/Citric Acid Trisodium di-hydrated 0.03M). The membranes were heated for 90 min. at 80° C., incubated in a pre-hybridisation solution (SSC 6×, Denhardt×s 10×, SDS 0,1%) at 55° C. for 90 min., and finally put overnight in a preheated hybridisation solution containing a specific radio-labelled oligonucleotide probe at 55° C. The hybridised membranes were washed 3 times in a SSC 6× solution at 55° C. for 10 min, dried and exposed on Kodak X-OMAT film overnight at −80° C.

The full length cDNA library was also analysed by sequencing a set of clones. The resulted DNA sequences were compared to EMBL/GenBank databases and were used to set up oligonucleotide probes to recover other corresponding clones. In this way, the complete consensus mRNA sequence of the SEQ.ID.NO.28 and 29 was confirmed by the recovery of two other clones corresponding to these sequences. Only one full-length cDNA clone corresponding to the subtractive clone 17 was isolated. Therefore, to identify the complete sequence of the SEQ.ID.NO.17 and SEQ.ID.NO.26, the Rapid Amplification of cDNA Ends (RACE) method was applied.

The RACE methodology was performed as described by Frohman et al. (1995). The reverse transcription step was carried out using 10 ng of mRNAs extracted from salivary glands of engorged ticks and the Thermoscript Reverse transcriptase (Life technologies, Rockville, Md., USA). All gene specific primers (GSP) had an 18 base length with a 61% G/C ratio. The amplified products were subjected to an agarose gel electrophoresis and recovered by using an isotachophorese procedure. The cDNAs were cloned into the pCRII-TOPO cloning vector (Invitrogen, Groningen, The Netherlands). To identify the consensus cDNA sequence, different clones were sequenced., and their sequence was compared to their known corresponding sequence. Therefore, the complete cDNA sequences of the clones 17 and 26 isolated in the subtractive library were obtained by this RACE procedure (FIG. 1).

Example 4

Analysis of the Full Sequences of 5 Selected Clones

The sequences of selected clones (SEQ.ID.NO.7, 17, 26, 31 and 33) allowed identification of the open reading frames, from which the amino sequence were deduced. These potential translation products have a size between 87 and 489 amino acids (see table 2). In order to evaluate, in silico, their respective properties, the amino acid sequences and the nucleotide sequences of said 5 open frames were compared with the databases using the tFasta and Blastp algorithms.

These comparisons show that SEQ.ID.NO.7 is highly homologous to the human Tissue Factor Pathway Inhibitor (TFPI). TFPI is an inhibitor of serine proteases having 3 tandemly arranged Kunitz-type-protease-inhibitor (KPI) domains. Each of these units or motifs has a particular affinity for different types of proteases. The first and second KPI domains are responsible for the respective inhibition of VIIa and Xa coagulation factors. The third KPI domain apparently has no inhibitory activity. It should be noted that the corresponding polypeptide sequence of SEQ.ID.NO.7 cDNA clone is homologous to the region of the first KPI domain of TFPI and that the KPI is perfectly kept therein. This similarity suggests that the SEQ.ID.NO.7 protein is a potential factor VIIa inhibitor.

The amino sequence deduced from the SEQ.ID.NO.28 clone has a great homology with 3 database sequences, namely: mouse TIS7 protein, rat PC4 protein and human SKMc15 protein. These 3 proteins are described as putative interferon type factors. They possess very well conserved regions of the B2 interferon protein. Therefore, it is proposed that the SEQ.ID.NO.31 protein has advantageous immunomodulatory properties.

Sequences SEQ.ID.NO.17 and SEQ.ID.NO.26 were compared with databases showing homology with the *Gloydius halys* (sub-order of ophidians) M12b metallopeptidase and the porcine elastase inhibitor belonging to the super-family of the serine protease inhibitors (Serpin), respectively. The amino sequences of these 2 clones also have specific motifs of said families. It is proposed that said proteins have advantageous anticoagulant and immuno-modulatory properties.

Finally, the SEQ.ID.NO.33 clone has a weak homology with the *R. norvegicus* leukocyte common antigen (LAR) that is an adhesion molecule. It is thus possible that the SEQ.ID.NO.33 protein has immunomodulatory properties related to those expressed by the LAR protein.

Due to their potential properties, most of the proteins examined are expected to be secreted in the tick saliva during the blood meal. Accordingly, tests were made for finding the presence of a signal peptide at the beginning of the deduced amino sequences. All of the results obtained with the Von Heijne analysis method were positive. By the McGeoch method, signal peptide sequences were detected for the SEQ.ID.NO.7, SEQ.ID.NO.17, SEQ.ID.NO.26 and SEQ.ID.NO.33 deduced amino sequences. It seems that said proteins are secreted in the tick salivary gland. Furthermore, the presence of a Kozak consensus sequence was observed upstream of the coding sequences of all examined clones. This indicates that their mRNAs potentially could be translated to proteins.

Example 5

Figure 2:
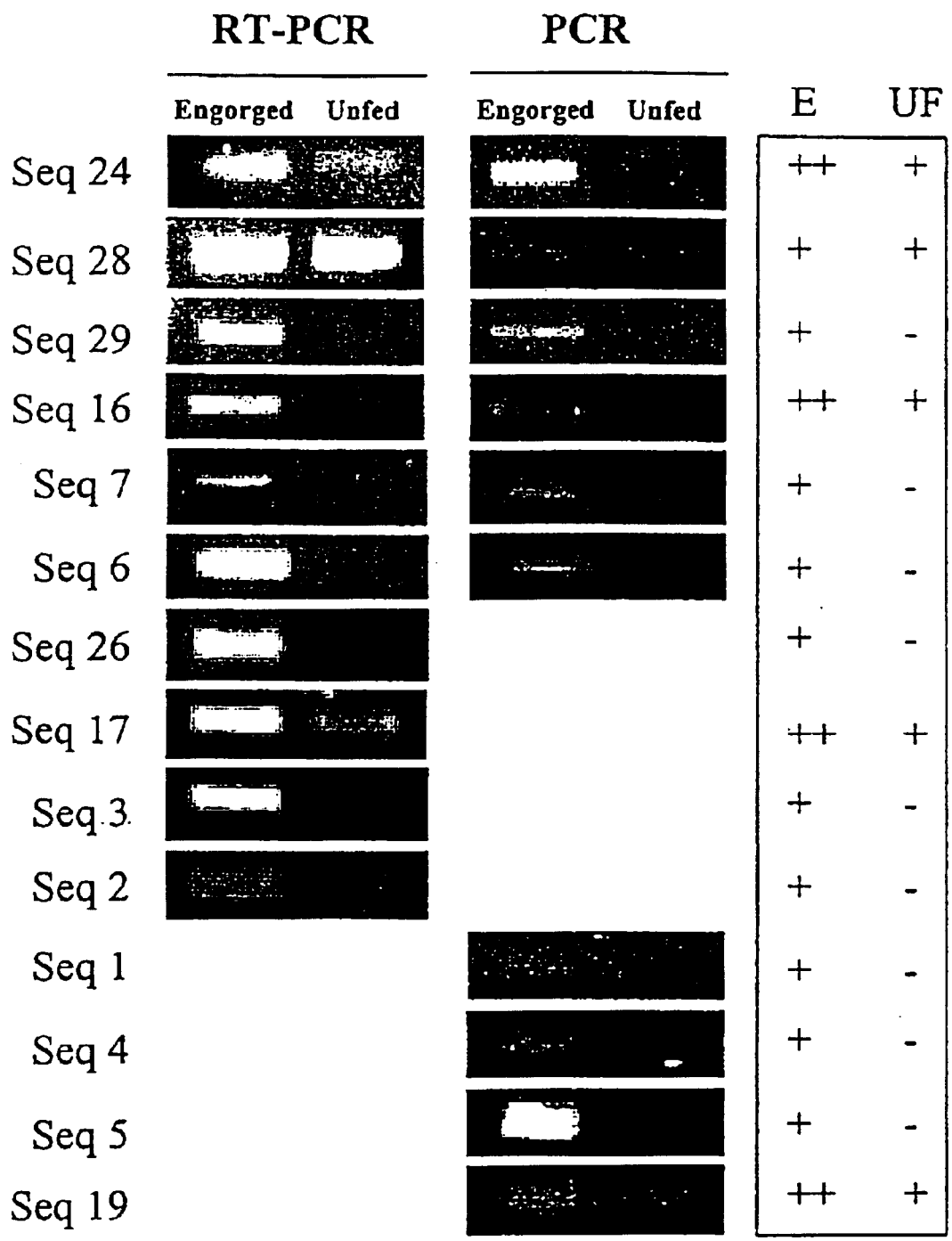
FIG. 2 represents differential expression analysis of the 5 full-length selected cDNAs and 9 cDNA fragments isolated in the subtractive library. PCR assays were carried out using as DNA template cDNAs obtained from a reverse transcription procedure on mRNAs extracted from salivary glands either of engorged (E) or of unfed (UF) ticks. These RNA messengers were also used as template in reverse transcription assays. Ten microliter of both PCR and RT-PCR mixture were subjected to agarose gel electrophoresis and ethidium bromide staining for the detection of amplified DNA products. [++] strongly positive; [+] positive; [−] negative.

Evaluation of the Differential Expression of the cDNA Clones Isolated in the Subtractive and Full-Length cDNA Libraries The differential expression of the mRNAs corresponding to the 5 full-length selected clones (SEQ. ID.NO.7,SEQ. ID.NO. 17, SEQ. ID.NO.26, SEQ. ID.NO.31 and SEQ.ID.NO.33) and of 9 subtractive clones was assessed using a PCR and a RT-PCR assays (FIG. 2).

The PCR assays were carried out using as DNA template cDNAs obtained from a reverse transcription procedure on mRNAs extracted from salivary glands either of engorged or of unfed ticks.

Each PCR assay included pair of primers specific to each target subtractive or cDNAs full-length sequence. PCR assays were performed in a final volume of 50 µl containing 20 pM primers, 0.2 mM deoxynucleotide (dATP, dCTP, dGTP and dTTP; Boehringer Mannheim GmbH, Mannheim, Germany), PCR buffer (10 mM TrisHCl,50 mM KCI, 2.5 mM. MgC12, pH 8.3) and 2.5 U of Taq DNA polymerase (Boehringer mannheim GmbH, Mannheim, Germany).

DNA samples were amplified for 35 cycles under the following conditions: 94 C for 1 min., 72 C for 1 min. and 64 C for 1 min, followed by a final elongation step of 72 C for 7 min.

The RT-PCR assay was carried out on the 5 selected full-length cDNA clones and on 5 cDNA subtractive clones. The mRNAs used as template in the reverse transcription assay was extracted from salivary glands of engorged and unfed *I. ricinus* ticks. The reverse transcription assays were performed using a specific primer (that target one the selected sequences) and the "Thermoscript Reverse transcriptase" (Life technologies, Rockville, Md., USA) at 60° C. for 50 min. Each PCR assay utilised the reverse transcription specific primer and an another specific primer. The PCR assays were performed in a final volume of 50 µl containing 1 µM primers, 0.2 mM deoxynucleotide (dATP, dCTP, dGTP and dTTP; Boehringer Mannheim GmbH, Mannheim, Germany), PCR buffer (10 mM Tris HCI, 50 mM KCl, 2.5 mM $MgCl_2$, pH 8.3) and 2.5 U of Expand High Fidelity polymerase (Roche, Bruxelles, Belgium). Single stranded DNA samples were amplified for 30 cycles under the following conditions: 95° C. for 1 min., 72° C. for 30 sec. and 60° C. for 1 min, followed by a final elongation step of 72° C. for 7 min.

The FIG. 2 shows that the expression of the selected sequences is induced in salivary glands of 5 day engorged ticks, except for the sequence 31 that is expressed at a similar level in salivary glands of engorged and unfed ticks. The expression of the other mRNAs could be either induced specifically or increased during the blood meal.

Example 6

Expression of Recombinant Proteins in Mammal Cells

The study of the properties of isolated sequences involves the expression thereof in expression systems allowing large amounts of proteins encoded by these sequences to be produced and purified.

The DNA sequences of the 5 selected clones (SEQ.ID.NO.7, SEQ.ID.NO.17, SEQ.ID.NO.26, SEQ.ID.NO.31 and SEQ.ID.NO.33) were transferred into the pCDNA3.1 His/V5 expression vector. Said vector allows the expression of heterologous proteins fused to a tail of 6 histidines as well as to the V5 epitope in eukaryotic cells. The different DNAs were produced by RT-PCR by using primers specific to the corresponding clones. These primers were constructed so as to remove the stop codon of each open reading frame or phase in order to allow the protein to be fused to the 6×HIS/Epitope V5 tail. In addition, the primers contained restriction sites adapted to the cloning in the expression vector. Care was taken to use, when amplifying, a high fidelity DNA polymerase (Pfu polymerase, Promega).

The transient expression of the Seq16 and 24 recombinant proteins was measured after transfection of the Seq16 and Seq24-pCDNA3.1-His/V5 constructions in COS1 cells, using Fugen 6 (Boehringer). The protein extracts of the culture media corresponding to times 24, 48 and 72 hours after transfection were analysed on acrylamide gel by staining with Coomassie blue or by Western blot using on the one hand an anti-6× histidine antibody or on the other hand Nickel chelate beads coupled to alcaline phosphatase.

These analyses showed the expression of said proteins in the cell culture media.

Example 7

Expression of Proteins in *E. coli*

7.1. Insertion of Coding Sequences into the pMAL-C2E Expression Vector.

Proteins fused with the Maltose-Binding-Protein (MBP) were expressed in bacteria by using the pMAL-C2E (NEB) vector. The protein of interest then could be separated from the MBP thanks to a site separating the MBP from the protein, said site being specific to protease enterokinase.

In order to express optimally the 5 sequences examined, using the pMAL-C2E vector, PCR primer pairs complementary to 20 bases located upstream of the STOP codon and to 20 bases located downstream of the ATG of the open reading frame or phase were constructed. The amplified cDNA fragments only comprise the coding sequence of the target mRNA provided with its stop codon. The protein of interest was fused to MBP by its N-terminal end. On the other hand, since these primers contained specific restriction sites specific to the expression vector, it was possible to effect direct cloning of the cDNAs. The use of Pfu DNA polymerase (Promega) made it possible to amplify the cDNAs without having to fear for errors introduced into the amplified sequences.

The coding sequences of clones SEQ.ID.NO.7, SEQ.ID.NO.17, SEQ.ID.NO.26 and SEQ.ID.NO.31 were reconstructed in that way. Competent TG1 cells of *E. coli* were transformed using these constructions. Enzymatic digestions of these mini-preparations of plasmidic DNA made it possible to check that the majority of clones SEQ.ID.NO.7, SEQ.ID.NO.17, SEQ.ID.NO.26 and 31-p-MALC2-E effectively were recombinant.

7.2. Expression of Recombinant Proteins.

Starting from various constructions cloned in TG1 *E. coli* cells, the study of the expression of recombinant proteins fused with MBP was initiated for all sequences of interest (i.e. SEQ.ID.NO.7, SEQ.ID.NO.17, SEQ.ID.NO.26 and SEQ.ID.NO.33) except for SEQ.ID.NO.31. The culture of representative clones of SEQ.ID.NO.7, SEQ.ID.NO.17, SEQ.ID.NO.26 and SEQ.ID.NO.33 as well as negative controls (non recombinant plasmids) were started to induce the expression of recombinant proteins therein. These cultures were centrifuged and the pellets were separated from the media for being suspended in 15 mM pH7.5 Tris and passed through the French press. The analysis of these samples on 10% acrylamide gel coloured with Coomassie blue or by Western Blot using rabbit anti-MBP antibodies, showed the expression of recombinant proteins SEQ.ID.NO.7 (~50 kDa), SEQ.ID.NO.17 (~92 kDa), SEQ.ID.NO.26 (~80 kDA) and SEQ.ID.NO.31 (~67 kDa).

Example 8

Production of Antibodies

The SEQ.ID.NO.7, SEQ.ID.NO.17 and SEQ.ID.NO.26 protein were injected into groups of 4 mice with the purpose of producing antibodies directed against said proteins. The antigens were firstly injected with the complete Freund adjuvant. Two weeks later, a recall injection was made with incomplete Freund adjuvant. The sera of mice injected with SEQ.ID.NO.17 provided positive tests for anti-MBP antibodies.

Example 9

Iris Protein Characterization

One clone, formerly named SEQ.ID.NO.26, was selected for further characterization of its recombinant protein, due to its similarity to the human thrombin inhibitor gene.

Using the RACE method, its complete cDNA sequence [Accession no: AJ269658] was recovered, and the complete ORF encodes a protein of 378 amino acids in length. Its comparison to EMBL/GenBank databases showed a high homology to the pig leukocyte elastase inhibitor, which shares a specific serine protease inhibitor motive. Based on the results, the Inventors have decided to call the tick protein SEQ.ID.NO.26 "Iris", for "*Ixodes Ricinus Immuno suppressor*".

Biological Materials.

Salivary glands of unfed (n=300) or 5 day engorged (n=70) pathogen free *I. ricinus* female adult ticks were collected by teasing them away from other internal organs. The salivary glands were crushed in an extraction buffer (PBS 1×, pH 7,4; EDTA 10 mM, AEBSF 1 mM—Sigma-Aldrich, Bornem, Belgium) for 10 min by using a potter and a pestle. The samples were centrifuged at 10,000 g for 8 min, and the supernatants were recovered and stored at −20° C.

Saliva was collected from 5 day engorged adult female ticks by using a finely drawn capillary tube fitted over the mouthparts of each tick. Before collecting saliva, each tick was washed with PBS 1× pH 7.2, and was injected with PBS 1× pH 7.2 containing a 0.2% dopamine (Sigma-Aldrich, Bornem, Belgium).

Production of Recombinant Iris Proteins (rIris) in Bacterial and Mammalian Expression Systems.

The screening of a RDA subtractive library identified iris cDNA. This library was constructed as described by Hubank and Schatz (Hubank et al, 1994) by using RNA messengers extracted from unfed and 5 day engorged tick salivary glands. The complete iris cDNA sequence was recovered by performing the RACE methodology as described by Frohman (Frohman, 1995). Two recombinant Iris proteins were synthesised: one in fusion with the maltose binding protein (rIris/MBP), and one in fusion with V5/His EpiTag (rIris/His). The recombinant rIris/MBP protein was expressed in *E. coli* by using the pMALC2-E vector (NEB, Hitchin, UK). The rIris/His protein was expressed in CHO-KI cells by using the pCDNA3.1/V5-His A vector in frame with the V5/His 6× EpiTag.

The rIris/His protein was also purified in batch by Ni-chelate chromatography (Ni-NTA superflow resin—Qiagen, Hilden, Germany) following the manufacturer's guidelines. Different buffers were used to purify the rIris/His protein: the lysis buffer (PBS 1×, NaCl 500 mM, Zwittergent 3.12 0.1%, pH7.5); the washing buffer (PBS 1×, NaCl 500 mM, Zwittergent 3.12 0.1%, imidazole 17.25 mM, pH 7.5), and the elution buffer (PBS 1×, NaCl 500 mM, Zwittergent 3.12 0.1%, imidazole 103 mM, pH 7.5). The eluate was dialysed (in a 7,000 Da cut-off membrane) in PBS 1×, NaCl 500 mM, pH 7.5. The concentration of rIris/His was evaluated on a Commassie blue stained acrylamide gel at ~10 ng/µl (250 nM), by comparison with known quantities of BSA.

Ten week-old female Balb/c mice were immunized with 5 μg of Seq.24/MBP in Freund's complete adjuvant. Three booster immunisations were carried out with the same amount of antigen in Freund's incomplete adjuvant, at 15-day intervals.

To examine the expression of native proteins in salivary glands and to detect rIris/His, the same quantities of fed and unfed tick salivary glands, and a rIris/His sample were subjected to SDS-PAGE and transferred onto nitrocellulose membranes. The membranes were probed with diluted sera directed against rIris/MBP (1:1,000) and revealed with NBT-BCIP.

*I. ricinus* salivary glands were isolated from unfed, 3 day and 5 day fed ticks, and were immobilised on silanated slides (Biorad, Nazareth EKE, Belgium). Salivary glands were fixed in a 4% paraformaldehyde solution for 30 min at room temperature. After a treatment with 0.5% Triton X-100, the samples were incubated in PBS 1×containing 5% FCS. The anti-rIris/MBP serum was used at a 1:10 dilution, and the secondary antibody, a FITC Anti-Mouse IgG (H+L) (ICN, Asse-Relegem, Belgium) at a 1:32 dilution. The slides were mounted in Vectashield mounting medium (Vector Lab, Peterborough, UK) and observed with a Leica confocal laser microscope by using a Leica TCS 4D operating system (Leica, Wetzlar, Germany).

Preparation of rIris/His Cellular and rIris Negative Control (NEG) Extracts for Immune Tests.

CHO-KI cells expressing rIris/His protein, obtained from a confluent culture in five 150 cm$^2$ flasks, were suspended in 1 ml of RPMI-1640 complete medium. The sample was frozen and thawed 3 times before being centrifuged at 50,000 g for 1 hour at 4° C. The supernatant was recovered and used in the different activity tests. The negative control (NEG) was a proteinic extract of CHO-KI cells resistant to G418 that do not express the recombinant protein and prepared as the rIris/His extract. The concentration of rIris/His in the cellular extract was evaluated at ~4 ng/μl (~100 nM), by comparing rIris/His contained in cellular extracts and purified rIris/His, on Western blot revealed with anti-V5 antibody (Invitrogen, Groningen, The Netherlands). The toxicity of the different samples for human PBMCs was evaluated by using the 7-AAD viability dye (Immunotech, Marseille, France), according to manufacturer's instructions.

Normal Balb/c Spleen Cells (SC):

A suspension of SC was obtained from normal Balb/c mice. 10$^6$ lymph node cells per well were cultivated for 2 hours in 100 μl of culture medium (RPMI-1640 (Gibco, Basel, Switzerland) supplemented with 10% fetal calf serum (v/v), 2 mM L-glutamin, 1 mM sodium pyruvate, 1 mM non-essential amino acids (Sigma, St Louis, Mo.), 0,05 mM mercaptoethanol, 100 U/ml penicillin/streptomycin (Gibco, Basel, Switzerland) and 25 μg/ml Funigizone—Gibco, Basel, Switzerland), with various dilutions of either rIris/His or NEG cellular extracts. Cells were stimulated with 10 μl of ConA (20 μg/ml) in a final volume of 200 μl for 15 hours. One μCi/well of [$^3$H]thymidine (Amersham Int., Amersham, UK) was added 24 hours before harvesting the cells. Tritiated thymidine incorporation was determined by liquid scintillation counting. Results showed the means of duplicate rIris/His or NEG stimulated wells realised in 2 independent experiments (+/− S.D.). Means of ConA-unstimulated wells were previously subtracted (net 10$^3$ c.p.m.).

Preinfested Balb/c Axiliary and Brachial Lymph Nodes Cells:

Axilary and brachial lymph nodes were removed from a mouse killed 9 days after infestation with 15 pathogen-free *I. ricinus* nymphs. 10$^6$ lymph nodes cells were cultured for 2 hours in 100 μl of complete RPMI-1640 medium. After 96 hours of incubation with various dilutions of rIris/His or NEG samples, 1 μCi/well of [$^3$H]thymidine (Amersham Int., Amersham, UK) was added 18–24 hours before harvesting the cells. Tritiated thymidine incorporation was determined by liquid scintillation counting.

Normal Human PBMCs:

Experiments were done with PBMCs obtained from 8 different donors. Cells were resuspended in RPMI-1640 medium supplemented with FCS 10% (v/v), L-glutamine 2 mM, penicilline-streptomycine (100 U/ml) and IL-2 (20 U/ml). 2.0 10$^6$ cells were pre-cultivated in 1 ml of culture medium. The cells were diluted at different concentrations in 96 wells plates: 2.0 10$^5$ cells/100 μl for Protein Purified Derivative (PPD) stimulation, 5.0 10$^4$ cells/100 μl for Lipopolysaccharides (LPS) stimulation for the ELIspot technique, and 2.0 10$^5$ cells/100 μl for the ELISA technique. Finally, PBMCs were incubated during 72 hours at 37° C. with various dilutions of rIris/His or NEG, in the presence or not of anti-rIris/MBP serum and different activators: Phytohaemmaglutinnin (PHA—at a final concentration of 1 μg/ml), LPS (1 μg/ml), CD3/CD28, (500 ng/ml), Phorbol Myristate Acetate (PMA)/CD28 (PMA 25 ng/ml—CD28 500 ng/ml) PPD (5 μg/ml).

ELIspot Assay:

96 wells nitrocellulose bottom coated plates (Multiscreen-HA Mahan, Millipore, Brussels, Belgium) were coated with coating antibodies directed against IFN-γ (clone C1-D16 MAB 1-D1K, Nodia, Antwerp, Belgium) and IL-10 (Clone JES3-9D7, BD Pharmingen, San Diego, Calif.). Cells were stimulated with PHA or LPS and S24p or S24n for 72 hours at 37° C. Supernatants were recovered and conserved at −20° C. before being analysed. The cytokines were detected with biotinylated anti-IFN-γ antibody (clone JES3-5A10 MAB 7-B6-1, Nodia, Antwerp, Belgium) and anti-IL10 antibody (clone JES3-12G8, BD Pharmingen, San Diego, Calif.) diluted in PBS Tween 0,25% (1 μg/ml). Finally, the plates were incubated with extravidine peroxydase and AEC substrate (Sigma-Aldrich, Bornem, Belgium). Results show the means of triplicate rIris/His or NEG cellular extracts stimulated wells (+/− S.D.). Means of unstimulated wells were previously subtracted.

ELISA Technique:

The different cytokines-specific ELISA were performed to detect of IFN-γ, IL-10, TNF-α, IL-6, IL-1β and IL-8. This was done by using the Flexia-human kit (Biosource, Nivelles, Belgium). In the case of the detection of IL-5, the IL-5 kit (Endogene, Woburn, Mass.) was used. The assays were carried out using manufacturer's instructions and were revealed using TMB substrate. The concentration of the different cytokines (pg/ml) was calculated by comparison to a standard curve generated with the different cytokines. Results show the means of rIris/His or NEG stimulated wells realised in 5 independent experiments (+/− S.D.). Means of unstimulated wells were previously subtracted.

Example 10

Detection of Iris in *I. ricinus* Salivary Glands and Saliva

Figure 3:
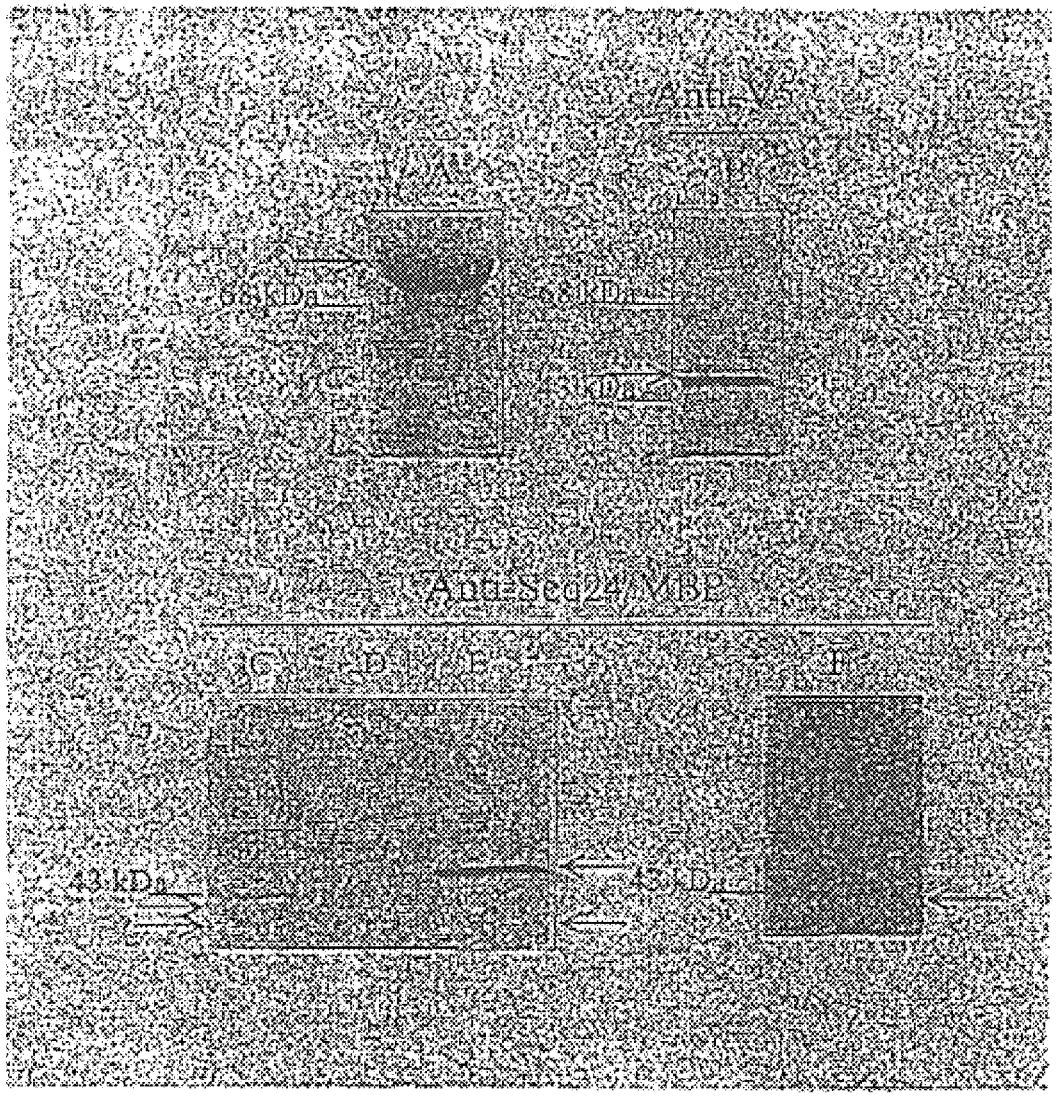
FIG. 3 relates to the detection of the native Iris (formerly named SEQ.ID.NO.26) protein by western blots using anti-rIris/MBP serum were realised on 5 day fed tick saliva.

Two recombinant Iris proteins were expressed either in *E. coli* cells using the pMALC2-E vector (NEB, Hitchin, UK) in fusion with the maltose binding protein (MBP) leading to the expression of a rIris/MBP 82 kDa fusion protein (FIG. 3) or in CHO-K1 cells by using the pCDNA3.1/V5-His A vector resulting in the expression of a rIris/His Tag fusion protein with a Mr of 43 kDa (FIG. 3). Immune sera recovered from mice injected with rIris/MBP were used to detect both rIris/His in CHO-K1 cells and the corresponding native Iris protein in unfed, in 3 day and 5 day fed female *I. ricinus* salivary glands. Recombinant and native proteins were detected on Western blots (FIG. 3). A similar double band pattern was revealed at ~46 kDa and 40 kDa (rIris/His) and at ~43 kDa and 40 kDa (native Iris) in CHO-KI extracts and in 5 day fed tick salivary glands, respectively. Interestingly, the protein was not detected in unfed tick salivary glands. Moreover, Iris was revealed in tick saliva at a molecular weight of 43 kDa.

Figure 4:
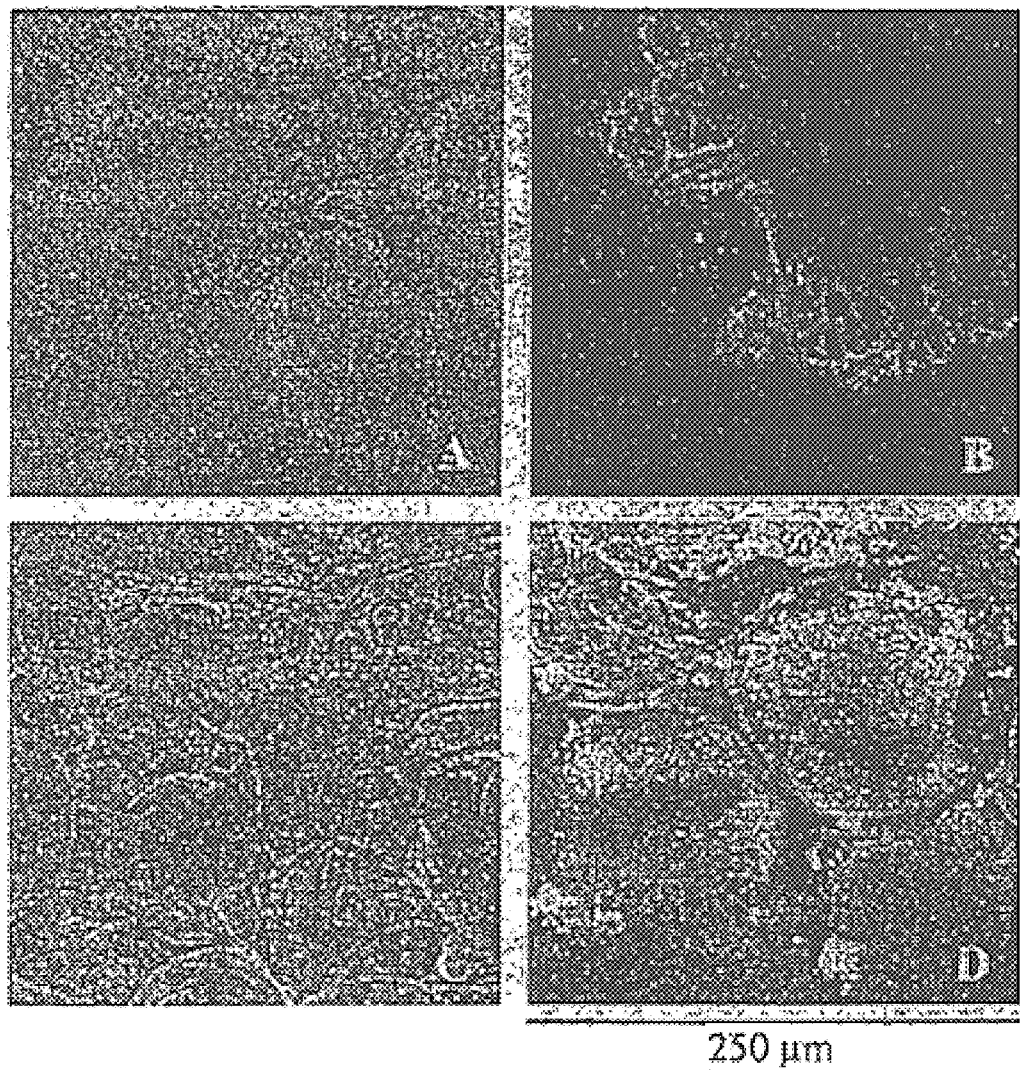
FIG. 4 represents results obtained by confocal microscopy of female *I. ricinus* salivary glands. A. Negative control corresponding to 5 day fed tick salivary glands incubated only with the secondary antibody. Unfed (B), 3 day (C) and 5 day (D) fed tick salivary glands incubated with the anti-rIris/MBP serum.

By using confocal microscopy, Iris was found in 3 day and, more abundantly, in 5 day fed tick salivary glands on the external surface of salivary acini, within the cells and also in the acini's light; but was not detected in unfed tick salivary glands (FIG. 4). All of these results infer that the expression of Iris is induced in the salivary glands during the tick feeding process and that Iris is secreted in tick saliva.

Example 11

Characterization of the Immunomodulatory Properties of Iris

Based on its homology to a neutrophil elastase inhibitor, the immunomodulatory properties of Iris were examined by using different activity tests that were mainly performed with soluble proteinic extracts of CHO-KI cells expressing rIris/His at a concentration of ~4 ng/µl (100 nM). Proteinic extracts of CHO-KI cells, which do not express rIris/His, were used as a negative control (NEG).

In Vitro Proliferation of Balb/c Normal Spleen Cells and Tick-Specific Lymph Nodes Cells.

Figure 5:
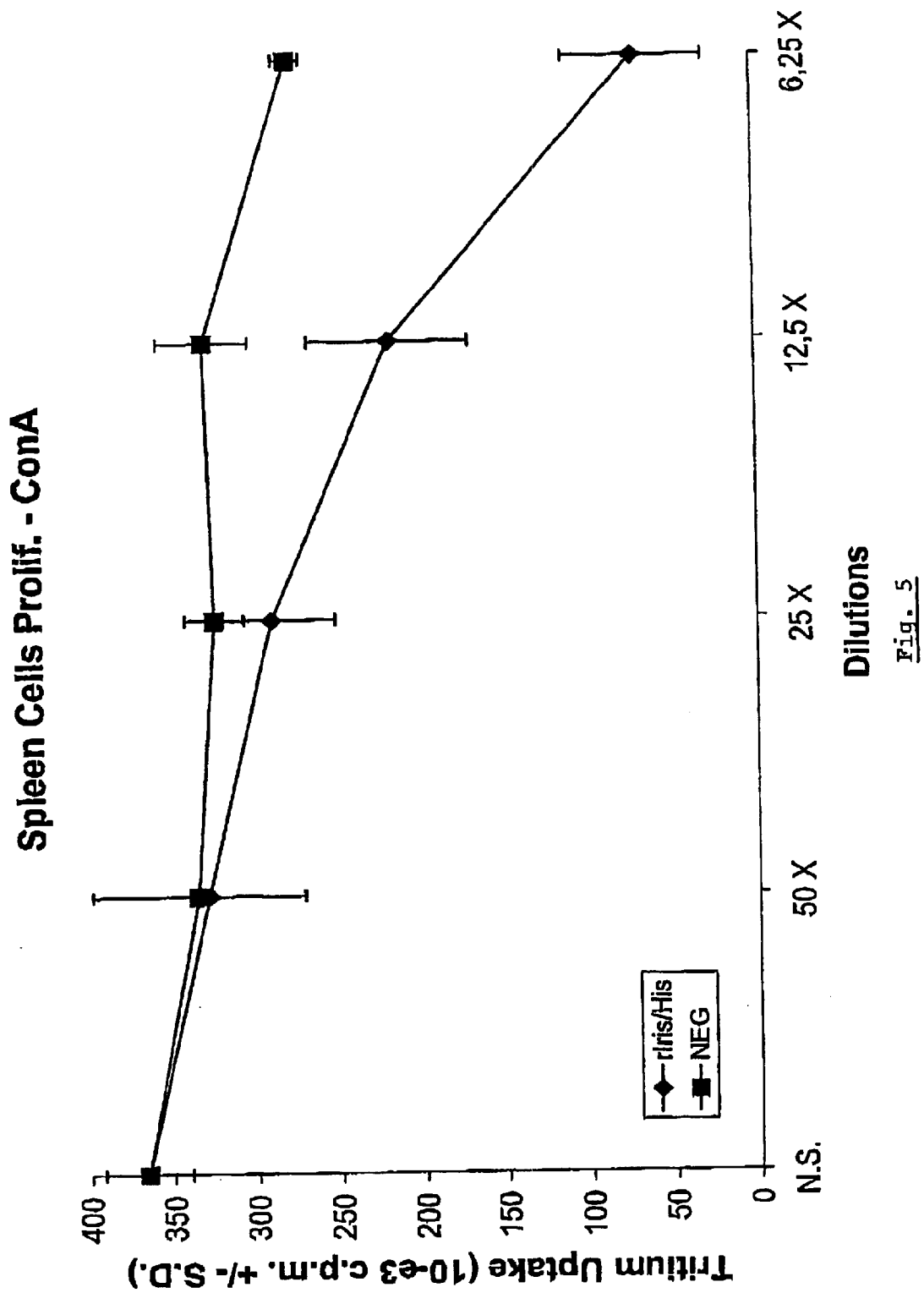
FIG. 5 represents in vitro proliferation assays of Balb/c spleen cells stimulated with ConA. Spleen cells were incubated with only ConA (N.S.) or with various dilutions of rIris/His and NEG cellular extracts. Tritiated thymidine incorporation was determined by liquid scintillation counting ($10^{-3}$ c.p.m. +/− S.D.).

The proliferation of normal Balb/c spleen cells (SC) was analysed in vitro by pre-incubating them with various dilution (1:6.25 to 1:50) of rIris/His cellular extracts, followed by stimulation with concanavaline-A (ConA). As shown on FIG. 5, the proliferative response of SC was strongly diminished (81% at dilution 1:6.25) in dose dependent concentration. The negative control had no significant effect on ConA-stimulated SC (average inhibition of 15%); even if this inhibited by 25% the SC proliferation at a 1:6.25 dilution.

Figure 6:
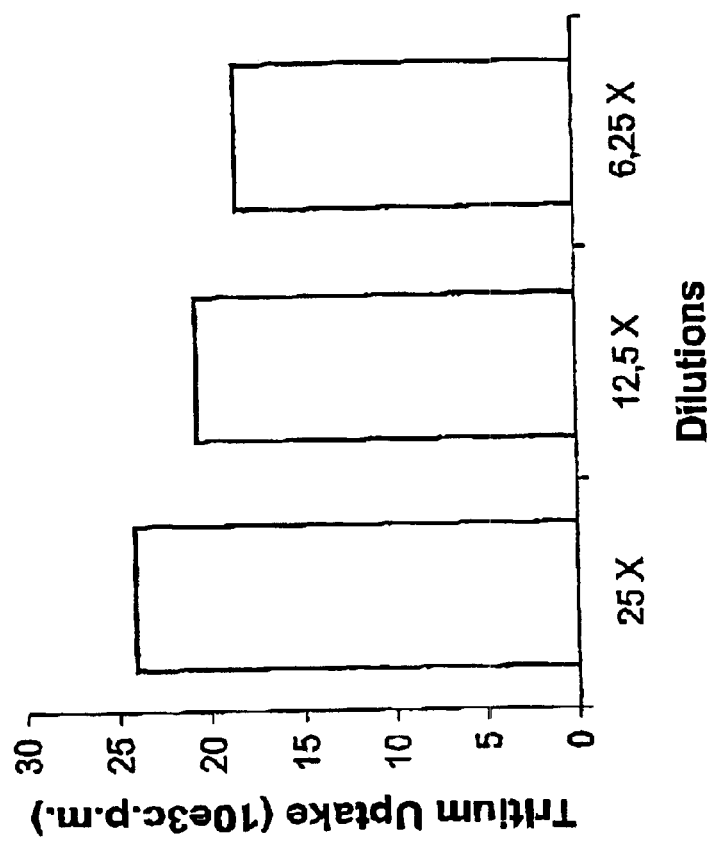
FIG. 6 presents Balb/c tick-specific lymph nodes cells proliferation assays. Lymph nodes cells were isolated from a mouse pre-infested with *I. ricinus* nymphs. Cells were stimulated with various dilutions of rIris/His and NEG cellular extracts. Tritiated thymidine incorporation was determined by liquid scintillation counting ($10^{-3}$ c.p.m.).
Figure 6:
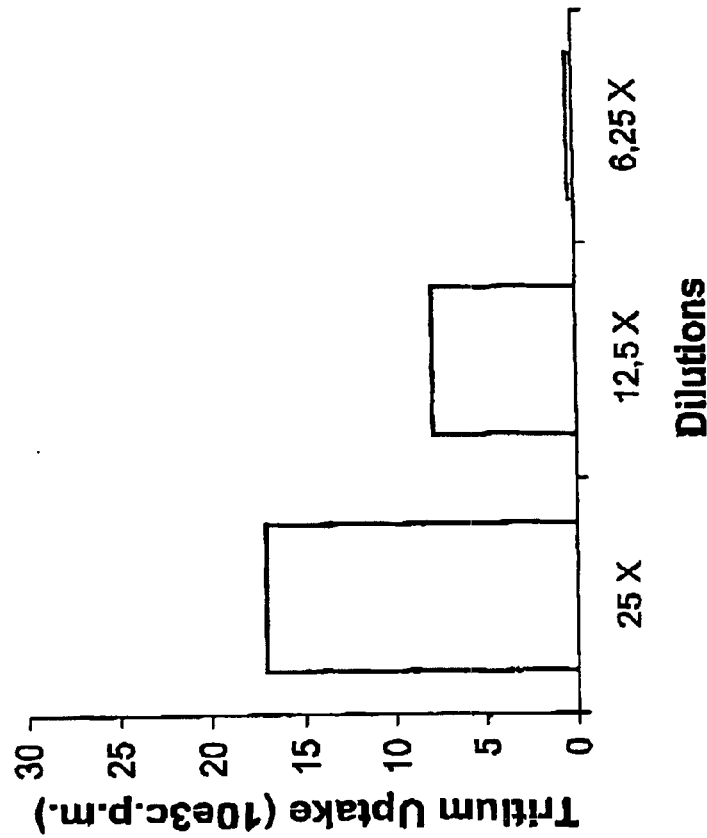

The immunogenicity of Iris was also studied by evaluating the proliferative responses of draining lymph node cells (LC) from one Balb/c mouse that was infected with 15 pathogen-free nymph *I. ricinus*. The isolated LC were incubated with increasing amount of both rIris/His and NEG protein extracts. The results indicated that in the presence of rIris/His, the proliferation of these LC was strongly inhibited in a dose dependent concentration (inhibition by 98.5% at dilution 1:6.25 in comparison to dilution 1:25, see FIG. 6). In contrast, the NEG protein extract had no significant effect on LC proliferation.

Example 12

In Vitro Cytokine Production by Human PBMCs

Figure 7:
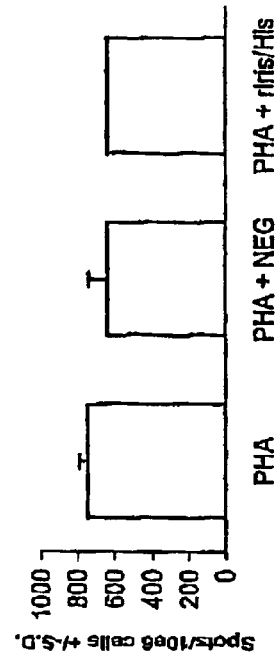
FIG. 7 refers to IFN-γ and IL-10 ELIspot of human PBMCs. The number of activated cells producing the cytokines upon treatment with PHA or LPS was evaluated (spots/$10^6$ cells +/− S.D.). Activated cells were counted after treatment with rIris/His or NEG cellular extracts. A positive control was realised by stimulating the cells only with the activator (PHA or LPS).
Figure 7:
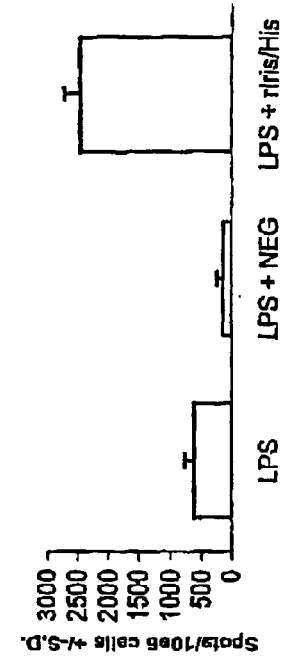
Figure 7:
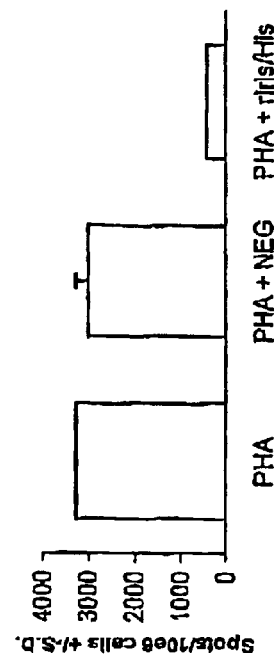
Figure 7:
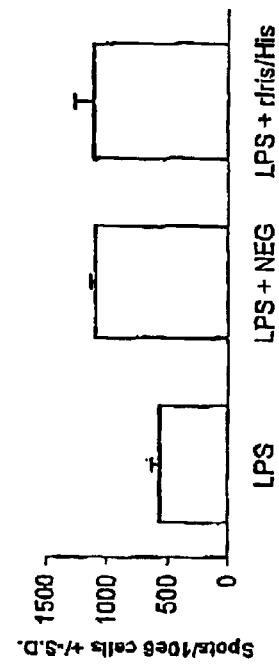

The effect of rIris/His on cytokine production was studied on human peripheral bone marrow cells (PBMCs) stimulated with different activators. The number of PBMCs secreting IFN-γ and IL-10, after stimulation either with lipopolysaccharides (LPS) or phytohaemagglutinin-A (PHA), was assayed by the ELISPOT technique (FIG. 7). Under PHA stimulation, in presence of rIris/His cellular extract, a reduced number of PBMCs (more than 80%) expressed IFN-γ while the number of cells producing IL-10 remained unchanged. The NEG protein extract had not effect on the production of both cytokines by PHA-stimulated PBMCs. In contrast, after LPS stimulation, no difference in the number of cells producing IFN-γ was observed between PBMCs incubated with rIris/His and the NEG cellular extract. On the other hand, rIris/His extract enhanced by 400% the number of PBMCs expressing IL-10, while stimulation with NEG cellular extract inhibited by 77% the number of cells producing IL-10.

The effect of the rIris/His cellular extract (used at a 1:5 dilution) on the production of cytokines (IFN-γ, IL-6, TNF-α, IL-10, IL-8 and IL-1β) by PBMCs stimulated with a set of activators (PHA, CD3/CD28, PMA/CD28, LPS and PPD) was also evaluated by ELISA (Table 3).

TABLE 3

Cytokine production by PBMC treated with rIris/his or NEG cellular extracts

| | Cell Stimulation | | | | | |
|---|---|---|---|---|---|---|
| | PHA | CD3/CD28 | PMA/CD28 | LPS | PPD | |
| IFN-γ | 36 | 46 | 8 | 43 | 6 | rIris/His |
| | 92 | 145 | 157 | 64 | 101 | NEG |
| expression | − | − | − | / | − | |
| IL-6 | 14 | 8 | 75 | 10 | 7 | rIris/His |
| | 88 | 95 | 84 | 195 | 61 | NEG |
| expression | − | − | / | − | − | |
| TNF-α | 12 | 525 | 53 | 10 | 15 | rIris/His |
| | 38 | 108 | 181 | 89 | 52 | NEG |
| expression | − | + | − | − | − | |
| IL-10 | − | 88 | − | 116 | 130 | rIris/His |
| | − | 101 | − | 27 | 98 | NEG |
| expression | / | / | / | + | / | |
| IL-8 | 5 | 7 | − | 0 | 0 | rIris/His |
| | 54 | 22 | − | 60 | 66 | NEG |
| expression | − | / | / | − | − | |

Values represent % of cytokine production calculated in comparison with cells stimulated only with the activator.
Expression is: inhibited (−), enhanced (+), unchanged or undefined (/).

Figure 8:
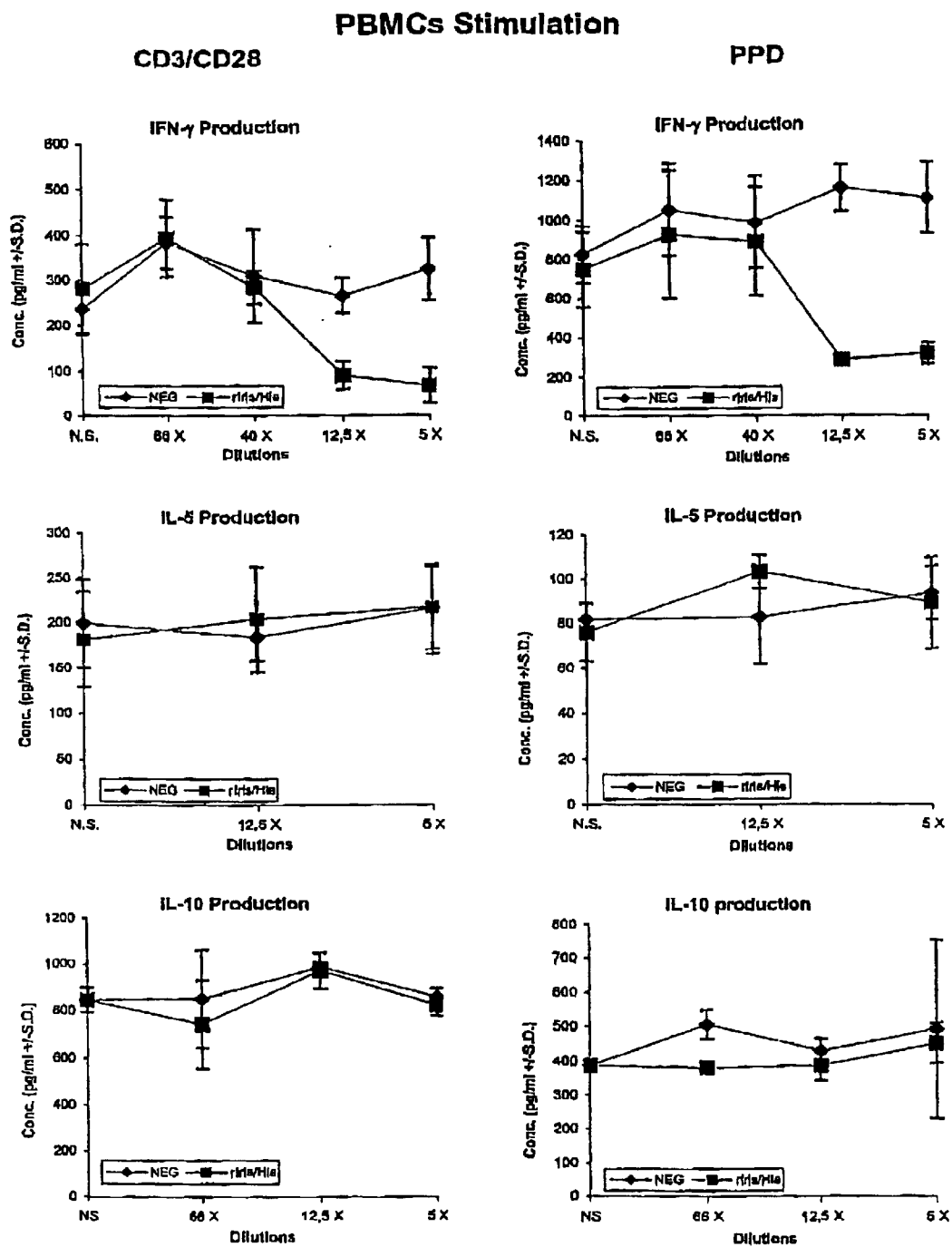
FIG. 8 relates to the IFN-γ and IL-5 production by human PBMCs. Cells were incubated with only the activator (N.S.) or with various dilutions of rIris/His and NEG cellular extracts. The production of IFN-γ and IL-5 (pg/ml +/− S.D.) was evaluated upon treatment with CD3/CD28 or PPD.

The results indicate that the production of almost all tested cytokines (IFN-γ, IL-6, TNF-α, IL-10, and IL-8) was inhibited by the rIris/His cellular extract, except for the IFN-γ production that was unaffected after LPS stimulation. Moreover, the production of IL-10 was not modulated after treatment with almost all activators, except under LPS stimulation, which slightly enhanced IL-10 production. In contrast, the NEG cellular extract had no significant effect on the cytokine production, except after LPS stimulation that inhibited the IL-10 production. Furthermore, it was shown that IL-1β production was unaffected by rIris/His cellular extract. The dose dependent effect of rIris/His was examined by analysing the IFN-γ, IL-5 and IL-10 production under CD3/CD28 and PPD stimulation (FIG. 8). In these cases, the maximum inhibition of IFN-γ production by rIris/His was of ~65% (P<0.01) and ~75% (P<0.05) after CD3/CD28 and PPD stimulation, respectively. This inhibition was still effective at a 1:12.5 dilution. In contrast, no difference in the production of IL-5 and IL-10 was observed between PBMCs incubated with rIris/His and NEG cellular extracts.

Figure 9:
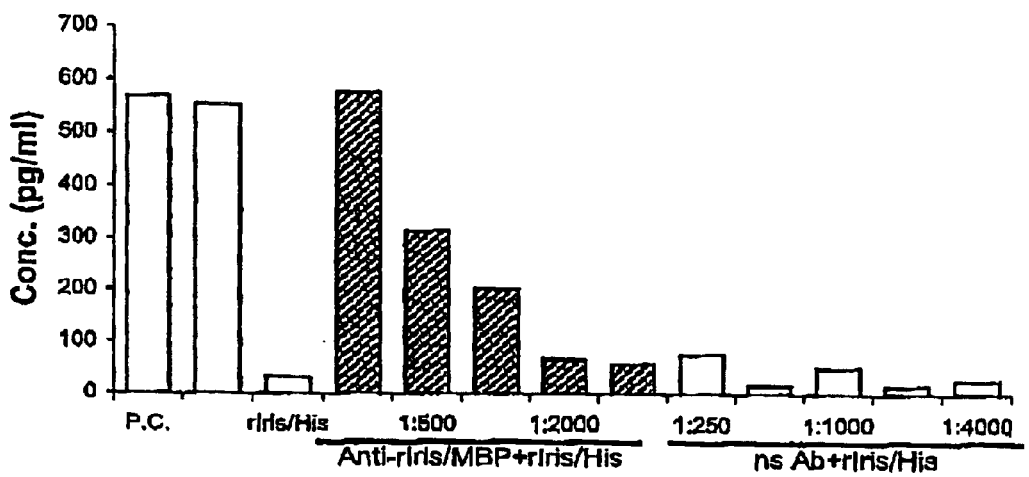
FIG. 9 represents IFN-γ production by human PBMCs stimulated with CD3/CD28. The cells were stimulated with NEG and rIris/His cellular extracts at a 1:12.5 dilution. All the assays were realized by stimulating the cells: only with CD3/CD28 (P.C.), with CD3/CD28 in the presence of NEG cellular extract (NEG), or with CD3/CD28 in the presence of rIris/His cellular extract (rIris/His). A. CD3/CD28 stimulated cells were incubated with rIris/His cellular extract in the presence of various dilutions of either anti-rIris/MBP serum (Anti-rIris/MBP+rIris/His) or a non-specific serum (ns Ab+rIris/His). B. CD3/CD28-stimulated cells were incubated with 400 nM CsA (CsA), with 400 nM CsA in the presence of anti-rIris/MBP serum (CsA+Anti-rIris/MBP), or with 400 nM CsA and the non-specific serum (CsA+NS AB); both antisera were used at a 1:250 dilution. C. CD3/CD28 stimulated PBMCs were also incubated with purified NEG (pNEG) or rIris/His (pIris/His) protein, and with purified NEG or rIris/His proteins in the presence of anti-rIris/MBP serum at a 1:250 dilution (pNEG+Anti-rIris/MBP and pIris/His+Anti-rIris/MBP).
Figure 9:
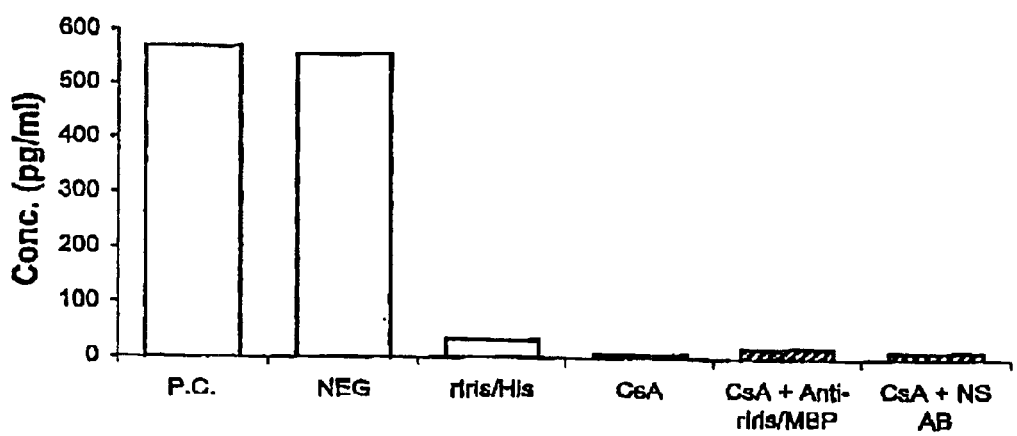
Figure 9:
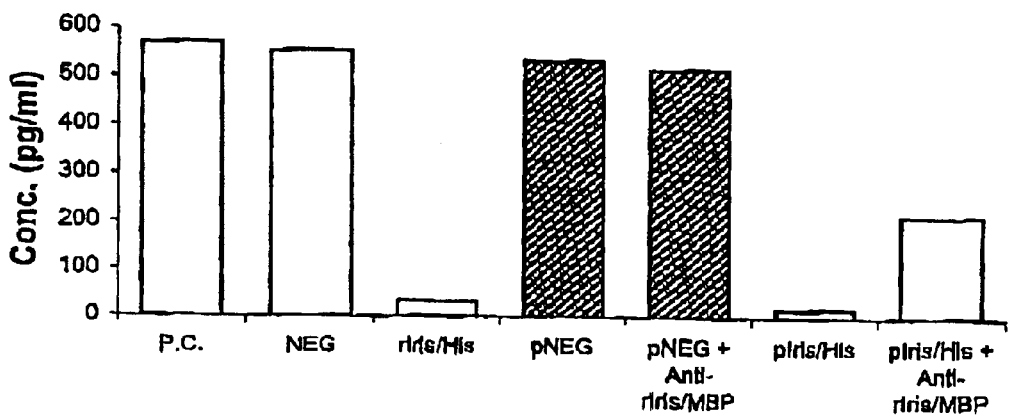

To confirm the role of Iris in the modulation of the production of some cytokines, PBMCs stimulated by CD3/CD28 activator were incubated with various dilutions (from 1:250 to 1:4,000) of anti-rIris/MBP serum (FIG. 9a). It was observed that PBMCs treated with rIris/His cellular extract (at dilution 1:12.5) in the presence of anti-rIris/MBP serum restored the IFN-γ production in a dose dependent manner (FIG. 9a); whilst this antiserum itself had no immunostimulating effect on cytokine production by the PBMCs.

At dilution 1:250, the antiserum re-established the IFN-γ production to a level similar to that obtained by CD3/CD28-stimulated PBMCs without the presence of rIris/His.

To assert the specificity of the neutralising activity of the anti-rIris/MBP serum, its effect was measured on the activity of cyclosporine-A (CsA) (FIG. 9b), an immunosuppressive drug. The effect of a serum specific to an unrelated MBP fusion protein was also measured on rIris/His cellular extracts activity (FIG. 9a). The anti-rIris/MBP serum (at a 1:250 dilution) did not affect the activity of 400 nM CsA, and the unrelated antiserum had no effect on the rIris/His immunomodulatory activity.

Finally, a small amount of rIris/His was purified from the rIris/His CHO-K1 cellular extract (FIG. 9c). This purified rIris/His protein, at a 25 nM concentration, completely inhibited the IFN-γ production by CD3/CD28-stimulated PBMCs, which was partially restored (50% of the IFN-γ production by CD3/CD28-stimulated PBMCs in absence of rIris/His) by using the anti-rIris/MBP serum at 1:250 dilution. Interestingly, it was found that the level of inhibition of ~25 nM of purified rIris/His was comparable to that of 400 nM CsA. The incubation of CD3/CD28-stimulated PBMCs with either a purified NEG or the anti-rIris/MBP (at 1:250 dilution) had no influence on the IFN-γ production.

It is now well established that the modulation of host immunity by tick saliva is of major importance in the successful accomplishment of the blood meal and in the transmission of tick-borne pathogens such as Borrelia burgdorferi, the causal agent of Lyme disease (Zeidner et al, 1996).

Although extensive information is available on the effects of tick feeding on host immune defenses, little is known about the nature of the immunomodulatory molecules expressed by tick salivary glands.

Tick salivary gland extracts (SGE) modulates host immune response by modifying the activity of several immune cells (lymphocytes, monocytes, macrophages, . . . ). An example of this is the inhibition of T lymphocyte proliferation in response to mitogens (Wikel, 1982) and the production of Th1 cytokines as IFN-γ and IL-2 by SGE (Ramachandra et al, 1992).

Moreover, Th2 type cytokine production such as IL-10, IL-5 and IL-4 is enhanced or remains unchanged (Ganapamo et al, 1995) (Ganapamo et al, 1996).

Tick SGE also inhibits the production of several cytokines (IFN-γ, IL-8, IL-6, TNF-α, . . . ) by human peripheral blood lymphocytes stimulated with LPS (Fuchsberger et al, 1995). Some studies indicated that these phenomena are induced by proteins (Urioste et al, 1994); (Schoeler et al, 2000); (Bergman et al, 2000).

The present invention has characterised the properties of a protein induced during the tick feeding process, which is called Iris for "Ixodes ricinus immunosuppressor", due to its exceptional properties. The corresponding mRNA sequence was first recovered by analysing a RDA subtractive library, and by using the RACE method.

In order to determine the immunomodulatory properties of Iris, the Inventors have studied the effect of the corresponding recombinant protein (rIris/His) on normal Balb/c spleen and lymph node cell proliferation, and on human PBMCs cytokine production, using specific T-lymphocytes (PHA, ConA, CD3/CD28 and PMA/CD28), macrophages (LPS) and antigen presenting cell—APC (PPD) activators. The results indicated that rIris/His cellular extracts inhibited the proliferation of murine lymphocytes on a dose dependent manner.

ELISA and ELIspot assays showed that the rIris/His cellular extracts suppressed the production of IFN-γ by TL and APC, while IL-5 and IL-10 level remained stable. In contrast, rIris/His extract did not affect IFN-γ production and enhanced the expression of IL-10 by macrophages.

It was also shown that the expression of the pro-inflammatory cytokines IL-6 and TNF-α by macrophages, TL, and APC was inhibited, while IL-1β expression remained unaffected.

Furthermore, by neutralising completely rIris/His cellular extract activity with a specific anti-rIris serum, and by showing that purified rIris/His protein inhibited IFN-γ production by T cells, it has been clearly established that the recombinant protein was effectively responsible of the immunomodulation.

Importantly, the inhibitory effect of ~25 nM rIris/His on IFN-γ production (inhibition of 94%) is comparable to 400 nM CsA activity (inhibition of 99%).

These observations indicate that Iris is a novel immuno-suppressor secreted by I. ricinus salivary glands into the saliva during the blood meal. It suppresses T lymphocyte proliferation and induces a Th2 type immune response that is characterised by the inhibition of IFN-γ production and an unaffected expression of IL-5 and IL-10. In addition, Iris modulates the mechanisms of innate immunity by inhibiting the production of pro-inflammatory cytokines (IL-6 and TNF-α).

It is known that several immunomodulatory factors are secreted in saliva at various times of the feeding process. Indeed, it was shown that SGE prepared daily from engorging ticks suppressed IL-1 production from day 0 to day 5 of engorgement while TNF-α production was suppressed during the entire blood meal (Ramachandra et al, 1992).

For this reason, it is suggested that Iris and other factors modulate host immunity at day 3 of engorgement. In contrast, from day 5 of engorgement, Iris is the only or the most important immunomodulatory factor, contained in tick saliva.

Finally, tick induced inhibition of IL-2, TNF-α and IFN-γ appears to facilitate B. burgdorferi survival in the vertebrate host, during the early phase of infection (Zeidner et al, 1996).

For this reason, based on its immune properties, Iris could be considered a major salivary factor that facilitates B. burgdorferi transmission.

REFERENCES

Ganapamo et al, 1997 Parasitology; 1997 Jul; 115 (Pt 1): 91–6
Ganapamo et al, 1995 Immunology; 1995 May; 85 (1): 120–4
Ganapamo et al, 1996 Immunology; 1996 Feb; 87 (2): 259–63
Wikel et al. 1996 Annu Rev-Entomol.; 1996; 41: 1–22
Wikel and Brossard, 1997 Med-Vet-Entomol.; 1997 Jul; 11 (3): 270–6
De Silva et al. 1995 Am. J. Trop. Med. Hyg.; 53(4), 1995 pp 397–404
Hubank and Schatz, 1994 Nucleic-Acids-Res.; Dec 25, 1994; 22 (25): 5640–8
Frohman. 1995: Rapid amplification of cDNA Ends. In PCR Primer. A laboratory manual (Dieffenbach, C. W. and Dveksler, G. S., eds), pp. 381–409, Cold Spring Harbor Laboratory Press, Cold Spring Harbor, N.Y.
Allen, J. R. (1973) Int. J. Parasitol., 3, 195–200.

Bergman, D. K. et al. (2000) *J. Parasitol.*, 86, 516–525.
Brossard, M. and Wikel, S. K. (1997) *Med. Vet. Entomol.*, 11, 270–276.
Frohman, B. H. (1995) Rapid amplification of cDNA ends. *PCR primer a laboratory manual.* Cold Spring Harbor Laboratory Press, pp. 381–469.
Fuchsberger, N. et al. *Exp. Appl. Acarol.*, 19, 671–676.
Ganapamo, F. et al. (1995) *Immunology*, 85, 120–124.
Ganapamo, F. et al. *Immunology*, 87, 259–263.
Hubank, M. and Schatz, D. G. (1994) *Nucleic Acids Res.*, 22, 5640–5648.
Kopecky, J. and Kuthejlova, M. (1998) *Parasite Immunol.*, 20, 169–174.
Ramachandra, R. N. and Wikel, S. K. (1992) *J. Med. Entomol.*, 29, 818–826.
Sauer, J. R. et al. (1995) *Annu. Rev. Entomol.*, 40, 245–267.
Schoeler, G. B. et al. *Ann. Trop. Med. Parasitol.*, 94, 507–518.
Urioste, S. et al. *J. Exp. Med.*, 180, 1077–1085.
Wang, H. and Nuttall, P. A. (1994) *Parasitology*, 109 (Pt 4), 517–523.
Wikel, S. K. (1982) *Ann. Trop. Med. Parasitol.*, 76, 627–632.
Zeidner, N. *J. Infect. Dis.*, 173, 187–195.

What is claimed is:

1. A isolated polypeptide encoded by a polynucleotide obtained from tick salivary gland said polynucleotide comprising a nucleotide sequence of SEQ ID NO: 26.

2. The isolated polypeptide according to claim 1, wherein said polypeptide is modified by or linked to at least one substitution group.

3. The isolated polypeptide of claim 1 in the form of a mature protein.

4. The isolated polypeptide of claim 1 as part of a larger protein.

5. The isolated polypeptide of claim 1 as part of a fusion protein.

6. The isolated polypeptide of claim 1 further including at least one additional amino acid sequence which contains secretory or leader sequences, pro-sequences, sequences which help in purification, or additional sequences for stability during recombination protection.

7. A pharmaceutical composition comprising an adequate pharmaceutical carrier and the polypeptide according to claim 1.

8. The pharmaceutical composition according to claim 7 which presents immunomodulatory properties.

9. An immunological composition or vaccine for inducing an immunological response in a mammalian host to a tick salivary gland polypeptide which comprises an isolated tick salivary gland polypeptide encoded by a polynucleotide comprising the nucleotide sequence SEQ. ID. NO.26.

10. A diagnostic kit for detecting a disease or susceptibility to a disease induced or transmitted by tick, especially *Ixodes ricinus*, which comprises an isolated tick salivary gland polypeptide encoded by a polynucleotide comprising the nucleotide sequence SEQ.ID.NO.26.

11. The isolated polypeptide of claim 6, wherein said sequences which help in purification comprise multiple histidine residues.

12. The isolated polypeptide of claim 2, wherein said at least one substitution group is selected from the group consisting of amide, acetyl, phosphoryl, and/or glycosyl groups.

* * * * *